(12) United States Patent
Bohlen et al.

(10) Patent No.: US 12,180,470 B2
(45) Date of Patent: Dec. 31, 2024

(54) SYSTEM AND METHOD FOR CELL TYPE-SPECIFIC TRANSLATION OF RNA MOLECULES IN EUKARYOTES

(71) Applicant: SRTD biotech GmbH, Cologne (DE)

(72) Inventors: Heribert Bohlen, Cologne (DE); Bernd Hoffmann, Jülich (DE)

(73) Assignee: SRTD BIOTECH GMBH, Cologne (DE)

( * ) Notice: Subject to any disclaimer, the term of this patent is extended or adjusted under 35 U.S.C. 154(b) by 462 days.

(21) Appl. No.: 16/487,377

(22) PCT Filed: Feb. 9, 2018

(86) PCT No.: PCT/EP2018/053241
§ 371 (c)(1),
(2) Date: Aug. 20, 2019

(87) PCT Pub. No.: WO2018/149740
PCT Pub. Date: Aug. 23, 2018

(65) Prior Publication Data
US 2020/0063131 A1  Feb. 27, 2020

(30) Foreign Application Priority Data
Feb. 20, 2017  (DE) .......................... 102017103383.1

(51) Int. Cl.
*C12N 15/113* (2010.01)
*C12N 15/67* (2006.01)
*C12N 15/79* (2006.01)

(52) U.S. Cl.
CPC ............ *C12N 15/113* (2013.01); *C12N 15/67* (2013.01); *C12N 15/79* (2013.01); *C12N 2310/11* (2013.01); *C12N 2310/50* (2013.01); *C12N 2840/203* (2013.01)

(58) Field of Classification Search
CPC ...... C12N 15/113; C12N 15/67; C12N 15/79; C12N 2310/11; C12N 2310/50; C12N 2840/203
See application file for complete search history.

(56) References Cited

U.S. PATENT DOCUMENTS

| | | | |
|---|---|---|---|
| 5,358,856 A | 10/1994 | Baltimore et al. |
| 5,766,903 A | 6/1998 | Sarnow et al. |
| 5,925,565 A | 7/1999 | Berlioz et al. |
| 6,060,273 A | 5/2000 | Dirks et al. |
| 6,096,505 A | 8/2000 | Selby et al. |
| 6,114,146 A | 9/2000 | Herlitschka et al. |
| 6,171,821 B1 | 1/2001 | Korneluk et al. |

FOREIGN PATENT DOCUMENTS

| | | | |
|---|---|---|---|
| JP | 2012023998 | * | 9/2012 |
| WO | 98/54342 | | 12/1998 |
| WO | 02/044321 | | 6/2002 |
| WO | 2015042184 A2 | | 3/2015 |
| WO | 2015042184 A3 | | 3/2015 |

OTHER PUBLICATIONS

KRT13 transcriptomics data, retrieved from https://www.proteinatlas.org/ENSG00000171401-KRT13/summary/rna (Year: 2022).*
Machine Translation of JP 2012023998 retrieved from https://patents.google.com/patent/JP2012023998A/en?oq=JP+2012023998+A+ (Year: 2012).*
Das et al.(Biotechnol. J. 2016, 11, 71-79) (Year: 2016).*
GTF2E1 transcriptomics data retrieved from https://www.proteinatlas.org/ENSG00000153767-GTF2E1/summary/ma (Year: 2022).*
J.R. Babendure et al., "Control of mammalian translation by mRNA structure near caps", RNA vol. 12, No. 5, pp. 851-861 (2006).
Mohammad Ali Faghihi et al., "Regulatory roles of natural antisense transcripts", Nature Reviews Molecular Biology, vol. 10, No. 9, pp. 637-643 (2009).
Munroe S. H. et al., "Overlapping transcripts, double-stranded RNA and antisense regulation: A genomic perspective", CMLS Cellular and Molecular Life Sciences, Birkhauser-Verlag, BA, vol. 63, pp. 2102-2118 (2006).
Flore Sinturel et al., "Cytoplasmic Control of Sense-Antisense mRNA Pairs", Cell Reports, vol. 12, pp. 1853-1864 (2015).
Pelechano et al., "Gene regulation by antisense transcription", Nature Reviews Genetics, vol. 14, pp. 880-893 (2013).
Kumar et al., "Antisense RNA: Function and Fate of Duplex RNA in Cells of Higher Eukaryotes", Microbiology and Molecular Biology Review, vol. 62, No. 4 (2018).
Ogawa et al., "Rational design of artificial riboswitches based on ligand-dependent modulation of internal ribosome entry in wheat germ extract and their applications as label-free biosensors", vol. 17, pp. 478-488 (2011).
Serganov et al., "A Decade of Riboswitches", Cell, vol. 152, pp. 17-24 (2013).
Standart et al., "MicroRNAs repress translation of m7Gppp-capped target mRNAs in vitro by inhibiting initiation and promoting deadenylation", Genes and Development, vol. 21, pp. 1975-1982 (2007).
Meister et al., "Mechanisms of gene silencing by double-stranded RNA", Nature, vol. 431, pp. 343-349, Sep. 16, 2004.
International Search Report and Written Opinion, International Patent Application No. PCT/EP2018/053241, May 9, 2018 with English translation (25 pages).
Ogawa, Atsushi, "Rational Design of Artificial ON-Riboswitches", Artificial Riboswitches: Methods and Protocols, Methods in Molecular Biology, vol. 1111, pp. 165-181 (2014).
"Tissue expression of GTF2E1—Summary—", The Human Protein Atlas, retrieved on the Internet on Jan. 24, 2024: https//www.proteinatlas.org/ENSG00000153767-GTF2E1/tissue, 4 pages.

(Continued)

*Primary Examiner* — Richard A Schnizer
(74) *Attorney, Agent, or Firm* — Merchant & Gould P.C.

(57) ABSTRACT

The present technology comprises methods and RNA constructs for the targeted translation of a polypeptide of interest in a eukaryotic target cell, and to the use thereof in therapeutic clinical applications.

14 Claims, 16 Drawing Sheets

Specification includes a Sequence Listing.

(56) References Cited

OTHER PUBLICATIONS

Tanaka, A. et al., "Homo sapiens general transcription factor IIE subunit 1 (GTF2E1), mRNA", GenBank, accession No. NM_005513.2, Oct. 6, 2016, 5 pages.
Office Action issued in Canadian Patent Application 3,054,096 (Apr. 2, 2024).

* cited by examiner

1 = CAP/modifications
2 = 5' UTR
3 = antisense fragment
4 = linker_IRES blocker_linker
5 = stem loops
6 = IRES (viral)
7 = sequence of interest
8 and 9 = 3' UTR and poly(A)

A)

1 = CAP/modifications
2 = 5'-UTR
3 = anticodogenic fragment
4 = linker_IRES blocker_linker
5 = stabilizing element
6 = IRES
7 = sequence of interest
8 and 9 = 3' UTR and poly(A)

Figure 4
A)
B) Secondary IRES sequence (6) rna.tbi.univie.ac.at/cgi-bin/RNAWebSuite/RNAprobing.cgi)
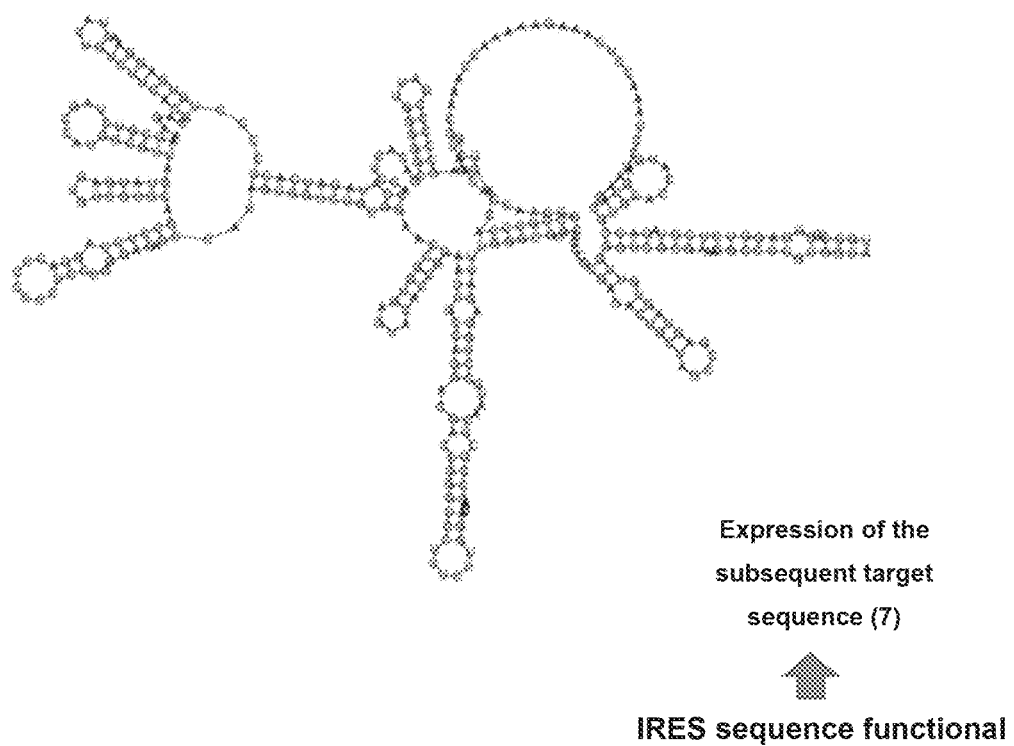
Expression of the subsequent target sequence (7)
⬆
IRES sequence functional

Figure 5

Primary IRES sequence (HCV IRES 1b); position 6 in Fig. 4: SEQ ID NO: 1

GCCAGCCCCCGATTGGGGGCGACACTCCACCATAGATCACTCCCCTGTGAGGAACTACTG
TCTTCACGCAGAAAGCGTCTAGCCATGGCGTTAGTATGAGTGTCGTGCAGCCTCCAGGAC
CCCCCCTCCCGGGAGAGCCATAGTGGTCTGCGGAACCGGTGAGTACACCGGAATTGCCAG
GACGACCGGGTCCTTTCTTGGATCAACCCGCTCAATGCCTGGAGATTTGGGCGTGCCCCC
GCGAGACTGCTAGCCGAGTAGTGTTGGGTCGCGAAAGGCCTTGTGGTACTGCCTGATAGG
GTGCTTGCGAGTGCCCCGGGAGGTCTCGTAGACCGTGCACCATGAGCACGAATCCTAAAC
CTCAAAGAAAAACCAAACGTAACACCAACCGCCGCCCACAGG

Figure 6
A)
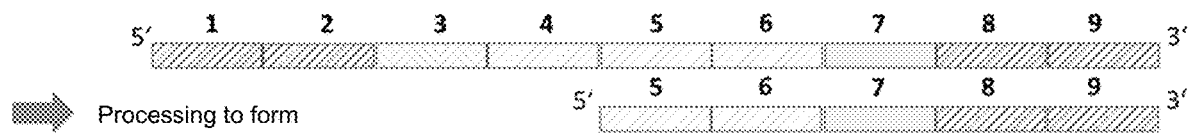
Processing to form
B) Secondary IRES sequence (6) with 3 stabilizing elements (5)
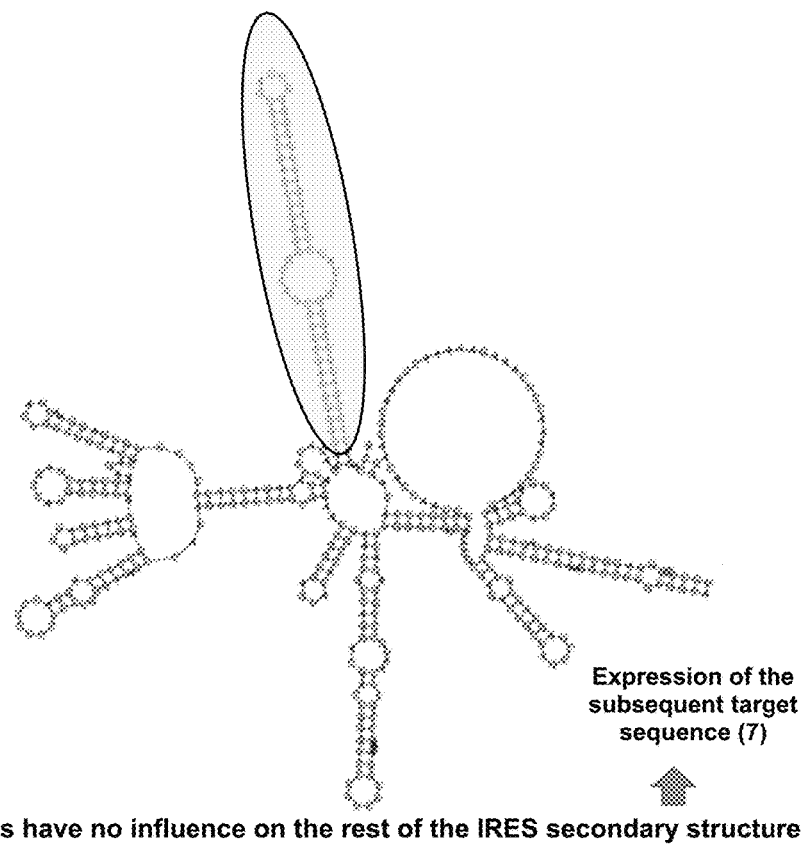
Expression of the subsequent target sequence (7)
Stabilizing elements have no influence on the rest of the IRES secondary structure

Figure 7

Primary IRES sequence (position 6 in Fig. 6) with 3 stabilizing elements (position 5 in Fig. 6): SEQ ID NO: 2

GCCAGCCCCGATTGGGGGGCCAGCCCCGATTGGGGGGCCAGCCCCGATTGGGGGGC
CAGCCCCGATTGGGGGCGACACTCCACCATAGATCACTCCCTGTGAGGAACTACTGTC
TTCACGCAGAAAGCGTCTAGCCATGGCGTTAGTATGAGTGTCGTGCAGCCTCCAGGACCC
CCCCTCCCGGGAGAGCCATAGTGGTCTGCGGAACCGGTGAGTACACCGGAATTGCCAGG
ACGACCGGGTCCTTTCTTGGATCAACCCGCTCAATGCCTGGAGATTTGGGCGTGCCCCCG
CGAGACTGCTAGCCGAGTAGTGTTGGGTCGCGAAAGGCCTTGTGGTACTGCCTGATAGGG
TGCTTGCGAGTGCCCCGGGAGGTCTCGTAGACCGTGCACCATGAGCACGAATCCTAAACC
TCAAAGAAAAACCAAACGTAACACCAACCGCCGCCCACAGG

Figure 8
A)
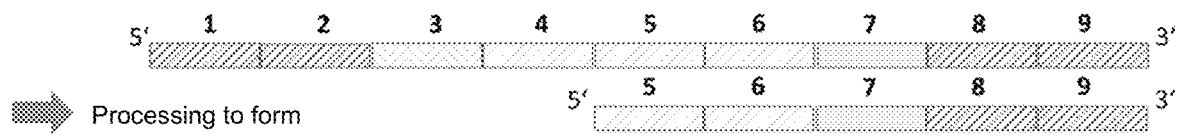
Processing to form
B) Secondary IRES sequence (6) with 3 stabilizing elements (5) and linkers (4a)
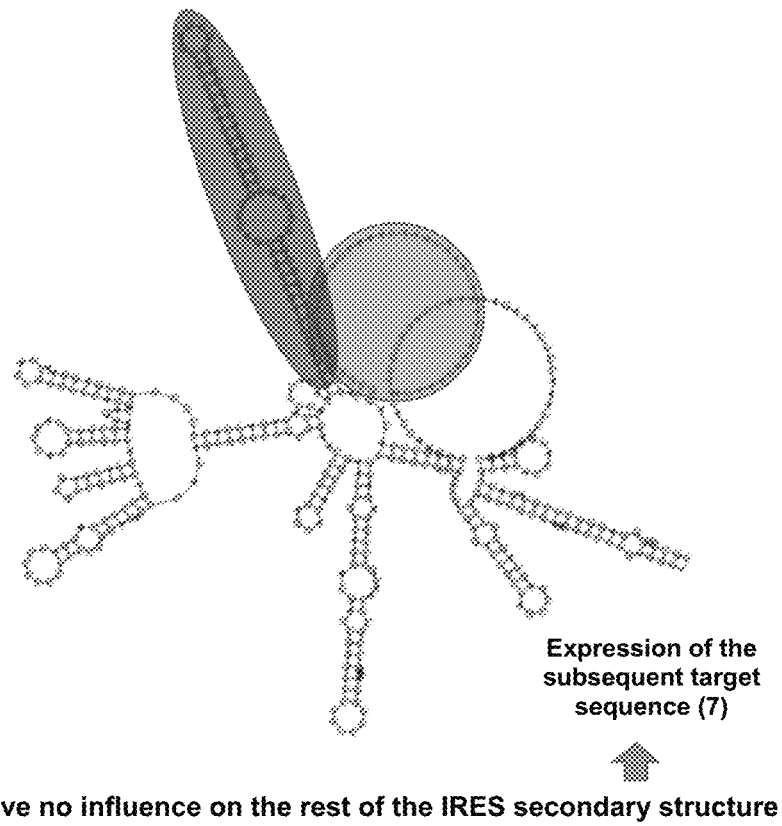
Expression of the subsequent target sequence (7)
Stabilizing elements have no influence on the rest of the IRES secondary structure

Figure 9

Primary IRES sequence (position 6 in Fig. 8) with 3 stabilizing elements (position 5 in Fig. 8, underlined) and linkers (position 4a in Fig. 8, boxed): SEQ ID NO: 3

ATAAATAAATAAATAAATAAATAAATAAATAAATAAAGCCAGCCCCGATTGGGGGG
CCAGCCCCGATTGGGGGGCCAGCCCCGATTGGGGGGCCAGCCCCGATTGGGGGCGA
CACTCCACCATAGATCACTCCCCTGTGAGGAACTACTGTCTTCACGCAGAAAGCGTCTAG
CCATGGCGTTAGTATGAGTGTCGTGCAGCCTCCAGGACCCCCCTCCCGGGAGAGCCATA
GTGGTCTGCGGAACCGGTGAGTACACCGGAATTGCCAGGACGACCGGGTCCTTTCTTGGA
TCAACCCGCTCAATGCCTGGAGATTTGGGCGTGCCCCCGCGAGACTGCTAGCCGAGTAGT
GTTGGGTCGCGAAAGGCCTTGTGGTACTGCCTGATAGGGTGCTTGCGAGTGCCCCGGGAG
GTCTCGTAGACCGTGCACCATGAGCACGAATCCTAAACCTCAAAGAAAAACCAAACGTA
ACACCAACCGCCGCCCACAGG

Figure 10
A)
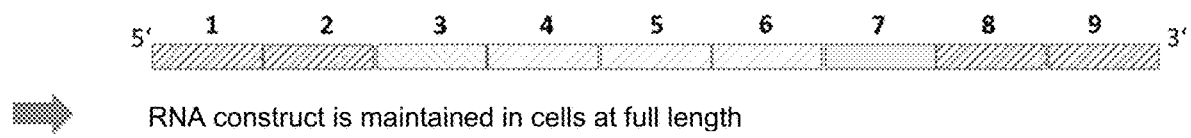
RNA construct is maintained in cells at full length
B) Secondary IRES sequence (6) with 3 stabilizing elements (5), linkers (4a) and blockers (4b)
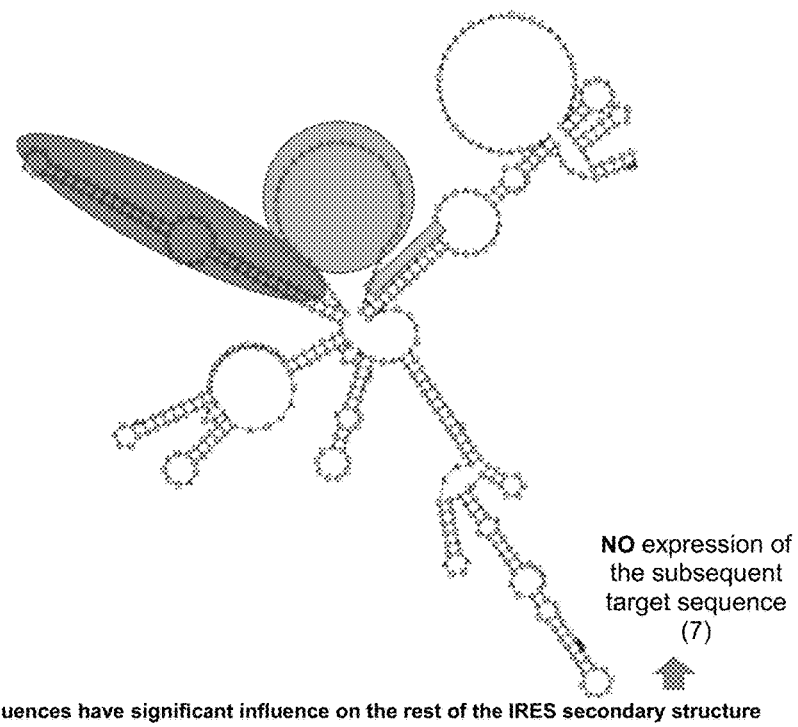
NO expression of the subsequent target sequence (7)
Even small blocker sequences have significant influence on the rest of the IRES secondary structure

Figure 11

Primary IRES sequence (position 6 in Fig. 10) with 3 stabilizing elements (position 5 in Fig. 10, underlined), linkers (position 4a in Fig. 8, boxed) and blockers (4b, bold): SEQ ID NO: 4

CCCAACACTATAAATAAATAAAATAAATAAATAAAATAAATAAATAAAGCCAGCCCCC
GATTGGGGGGCCAGCCCCCGATTGGGGGGCCAGCCCCCGATTGGGGGGCCAGCCCCGA
TTGGGGGCGACACTCCACCATAGATCACTCCCTGTGAGGAACTACTGTCTTCACGCAGA
AAGCGTCTAGCCATGGCGTTAGTATGAGTGTCGTGCAGCCTCCAGGACCCCCCTCCCGG
GAGAGCCATAGTGGTCTGCGGAACCGGTGAGTACACCGGAATTGCCAGGACGACCGGGT
CCTTTCTTGGATCAACCCGCTCAATGCCTGGAGATTTGGGCGTGCCCCGCGAGACTGCT
AGCCGAGTAGTGTTGGGTCGCGAAAGGCCTTGTGGTACTGCCTGATAGGGTGCTTGCGAG
TGCCCCGGGAGGTCTCGTAGACCGTGCACCATGAGCACGAATCCTAAACCTCAAAGAAA
AACCAAACGTAACACCAACCGCCGCCCACAGG

Figure 12

Selective mRNA expression system with short antisense sequence

| Short Keratin 13 | 80 bp |
|---|---|
| Loops | 225 bp |
| IRES | 577 bp |
| eGFP | 716 bp |
| skLIG | 2063 bp |

Recognition sites:

| ACCGGT | AgeI |
|---|---|
| GAATTC | EcorI |
| GCGGCCGC | NotI |
| GGATCC | BamHI |
| TCTAGA | XbaI |
| GTCGAC | Sal1 | short KERATIN

ACCGGTCGGCCTCCTCCCAGCTGGCAAGAGCCACCCCGAAACCACCTCCATAGCTGGCAGAGGAGCTCTGCAGGCGGAGGCTCATGAATTCGTTATGTTATGACCTTGCTCGTCAAGAAGACAGTTATGTTAT

*LOOP*

*TAAAAGTCAGGTCGGATCAAGCCATAGTACGGAAAAAACTATGCTACCTGTGAGCCCCGTCCAAGGACGTGCGGCCGC*TAAAAGAAGTCAGGCCATCA*CAAATGCCACAGCTTGAGTAAACTGTGCAGCCTGTAGCTCCACCTGAGAAGGTGTAAAAAA*GTTATGTTAT

GGATCCCCCCCCTAACGTTACTGGCCGAAGCCGCTTGGAATAAGGCCGGTGTGCGTTTGTCTATATGTTATTTTCCACCATATTGCCGTCTTTTGGCAATGTGAGGGCCCGGAAACCTGGCCCTGTCTTCTTGACGAGCATTCCTAGGGGTCTTTCCCCTCTCGCCAAAGGAATGCAAGGTCTGTTGAATGTCGTGAAGGAAGCAGTTCCTCTGGAAGCTTCTTGAAGACAAACAACGTCTGTAGCGACCCTTTGCAGGCAGCGGAACCCCCCACCTGGCGACAGGTGCCTCTGCGGCCAAAAGCCACGTGTATAAGATACACCTGCAAAGGCGGCACAACCCCAGTGCCACGTTGTGAGTTGGATAGTTGTGGAAAGAGTCAAATGGCTCTCCTCAAGCGTATTCAACAAGGGGCTGAAGGATGCCCAGAAGGTACCCCATTGTATG

IRE

GGATCTGATCTGGGGCCTCGGTGCACATGCTTTACATGTGTTTAGTCGAGGTTAAAAAACGTCTAGGCCCCCGAACCACGGGGACGTGGTTTTCCTTTGAAAAACACGATGATAATATGGCCACAACCATGTCTAGA

ATGGTGAGCAAGGGCGAGGAGCTGTTCACCGGGGTGGTGCCCATCCTGGTCGAGCTGGACGGCGACGTAAACGGCCACAAGTTCAGCGTGTCCGGCGAGGGCGAGGGCGATGCCACCTACGGCAAGCTGACCCTGAAGTTCATCTGCACCACCGGCAAGCTGCCCGTGCCCTGGCCCACCCTCGTGACCACCCTGACCTACGGCGTGCAGTGCTTCAGCCGCTACCCCGACCACATGAAGCAGCACGACTTCTTCAAGTCCGCCATGCCCGAAGGCTACGTCCAGGAGCGCACCATCTTCTTCAAGGACGACGGCAAC eGF

TACAAGACCCGCGCCGAGGTGAAGTTCGAGGGCGACACCCTGGTGAACCGCATCGAGCTGAAGGGCATCGACTTCAAGGAGGACGGCAACATCCTGGGGCACAAGCTGGAGTACAACTACAACAGCCACAACGTCTATATCATGGCCGACAAGCAGAAGAACGGCATCAAGGTGAACTTCAAGATCCGCCACAACATCGAGGACGGCAGCGTGCAGCTCGCCGACCACTACCAGCAGAACACCCCCATCGGCGACGGCCCCGTGCTGCTGCCCGACAACCACTACCTGAGCACCCAGTCCGCCCTGAGCAAAGACCCCAACGAGAAGCGCGATCACATGGTCCTGCTGGAGTTCGTGACCGCCGCCGGGATCACTCTCGGCATGGACGAGCTGTACAAGTAAGTCGAC

Figure 13

Selective mRNA expression system with long antisense sequence

| | |
|---|---|
| Keratin 13 | 625 bp |
| Loops | 225 bp |
| IRES | 577 bp |
| eGFP | 716 bp |
| KLIG | 2143 bp |

Recognition sites:

| | |
|---|---|
| ACCGGT | AgeI |
| GAATTC | EcorI |
| GCGGCCGC | NotI |
| GGATCC | BamHI |
| TCTAGA | XbaI |
| GTCGAC | SalI |

KERATIN:
ACCGGTTGATGTCGGCCTCCACGCTCTGGCGCAGGGCCAGCTCATTCTCATACTTGAG
CCTGAAGTCGTCCGCAGCCAGCCTGGCATTGTCAATCTCCAGGATGACCCGGTTGTTT
TCAATGGTGGCGGTCAGGATCTTGTCCCGGAGCTCTTCAATGGTCTTGTAGTAGGGGC
TGTAGTCCCGCTCAGGGCTAGCTGGGCTCTGCTTCAGGTGCCAGTCACGGATCTTCAC
CTCCAGGTCAGCGTTGGCCTCCTCCAGGGCGCGCACCTTCTCCAGGTAGGAAGCCAG
GCGGTCGTTGAGGTTCTGCATGGTGATCTTCTCATTGCCAGTGAGGAGGCCGCCATCA
CAAGCACCAAAGTCAACAAAGCCACCAGCAAAACCCCCACCAAAGCCACCTCCAAG
GCCACCTCCATAGCCACCTCCAAGGCCACCTCCATAGCCACCTCCAAAGCCACTACC
AGCCCCTCCACCAAAACCACAGCTCACGCCGCCTCCATAGCCCCCAGCTGATCCCCC
AGACACAAACCGAGTTGAACAGGTAGAGACACCACGGCCTCCTCCCAGCTGGCAAG
AGCCACCCCGAAACCACCTCCATAGCTGGCAGAGGAGCTCTGCAGGCGGAGGCTC
ATGAATTCGTTATGTTATGACCTTGCTCGTCAAGAAGACAGTTATGTTAT*TAAAAGTCA*

LOOP:
*GGTCGGATCAAGCCATAGTACGGAAAAAACTATGCTACCTGTGAGCCCCGTCCAAGGA
CGTGCGGCCGCTAAAAGAAGTCAGGCCATCACAAATGCCACAGCTTGAGTAAACTGTG
CAGCCTGTAGCTCCACCTGAGAAGGTGTAAAAAA*GTTATGTTATGGATCCCCCCCCTAA

IRES:
CGTTACTGGCCGAAGCCGCTTGGAATAAGGCCGGTGTGCGTTTGTCTATATGTTATTTT
CCACCATATTGCCGTCTTTTGGCAATGTGAGGGCCCGGAAACCTGGCCCTGTCTTCTT
GACGAGCATTCCTAGGGGTCTTTCCCCTCTCGCCAAAGGAATGCAAGGTCTGTTGAAT
GTCGTGAAGGAAGCAGTTCCTCTGGAAGCTTCTTGAAGACAAACAACGTCTGTAGCG
ACCCTTTGCAGGCAGCGGAACCCCCACCTGGCGACAGGTGCCTCTGCGGCCAAAA
GCCACGTGTATAAGATACACCTGCAAAGGCGGCACAACCCCAGTGCCACGTTGTGAG
TTGGATAGTTGTGGAAAGAGTCAAATGGCTCTCCTCAAGCGTATTCAACAAGGGGCTG
AAGGATGCCCAGAAGGTACCCCATTGTATGGGATCTGATCTGGGGCCTCGGTGCACA
TGCTTTACATGTGTTTAGTCGAGGTTAAAAAACGTCTAGGCCCCCGAACCACGGGGA
CGTGGTTTTCCTTTGAAAAACACGATGATAATATGGCCACAACCATGTCTAGAATGGT eGFP:
GAGCAAGGGCGAGGAGCTGTTCACCGGGGTGGTGCCCATCCTGGTCGAGCTGGACG
GCGACGTAAACGGCCACAAGTTCAGCGTGTCCGGCGAGGGCGAGGGCGATGCCACC
TACGGCAAGCTGACCCTGAAGTTCATCTGCACCACCGGCAAGCTGCCCGTGCCCTGG
CCCACCCTCGTGACCACCCTGACCTA

Figure 14

Selective mRNA expression system with alternative blocker sequence and long antisense sequence

| Keratin 13 | 625 bp |
|---|---|
| Loops | 225 bp |
| IRES | 577 bp |
| eGFP | 716 bp |
| KLIG | 2143 bp |

Recognition sites:

| ACCGGT | AgeI |
|---|---|
| GAATTC | EcorI |
| GCGGCCGC | NotI |
| GGATCC | BamHI |
| TCTAGA | XbaI |
| GTCGAC | SalI |

KERATIN

ACCGGTTGATGTCGGCCTCCACGCTCTGGCGCAGGGCCAGCTCATTCTCATACTTGAGCCTGA
AGTCGTCCGCAGCCAGCCTGGCATTGTCAATCTCCAGGATGACCCGGTTGTTTTCAATGGTGGC
GGTCAGGATCTTGTCCCGGAGCTCTTCAATGGTCTTGTAGTAGGGGCTGTAGTCCCGCTCAGG
GCTAGCTGGGCTCTGCTTCAGGTGCCAGTCACGGATCTTCACCTCCAGGTCAGCGTTGGCCTC
CTCCAGGGCGCGCACCTTCTCCAGGTAGGAAGCCAGGCGGTCGTTGAGGTTCTGCATGGTGAT
CTTCTCATTGCCAGTGAGGAGGCCGCCATCACAAGCACCAAAGTCAACAAAGCCACCAGCAAA
ACCCCCACCAAAGCCACCTCCAAGGCCACCTCCATAGCCACCTCCAAGGCCACCTCCATAGCC
ACCTCCAAAGCCACTACCAGCCCCTCCACCAAAACCACAGCTCACGCCGCCTCCATAGCCCCC
AGCTGATCCCCAGACACAAACCGAGTTGAACAGGTAGAGACACCACGGCCTCCTCCCAGCT
GGCAAGAGCCACCCCGAAACCACCTCCATAGCTGGCAGAGGAGCTCTGCAGGCGGAGGCTC
ATGAATTCGTTATGTTATGAACTGCTTCCTTCACGACATTCAACAGACCTTGTTATGTTATTAAAAG eGFP

TCAGGTCGGATCAAGCCATAGTACGGAAAAAACTATGCTACCTGTGAGCCCCGTCCAAGGACGT
GCGGCCGC*TAAAAGAAGTCAGGCCATCACAAATGCCACAGCTTGAGTAAACTGTGCAGCCTGTA*
*GCTCCACCTGAGAAGGTGTAAAAAA*GTTATGTTATGGATCCCCCCCCTAACGTTACTGGCCGAA

LOOP

GCCGCTTGGAATAAGGCCGGTGTGCGTTTGTCTATATGTTATTTTCCACCATATTGCCGTCTTTT
GGCAATGTGAGGGCCCGGAAACCTGGCCCTGTCTTCTTGACGAGCATTCCTAGGGGTCTTTCC
CCTCTCGCCAAAGGAATGCAAGGTCTGTTAATGTCGTGAAGGAAGCAGTTCCTCTGGAAGCT
TCTTGAAGACAAACAACGTCTGTAGCGACCCTTTGCAGGCAGCGGAACCCCCCACCTGGCGAC
AGGTGCCTCTGCGGCCAAAAGCCACGTGTATAAGATACACCTGCAAAGGCGGCACAACCCCA

IRE

GTGCCACGTTGTGAGTTGGATAGTTGTGGAAAGAGTCAAATGGCTCTCCTCAAGCGTATTCAAC
AAGGGGCTGAAGGATGCCCAGAAGGTACCCCATTGTATGGGATCTGATCTGGGGCCTCGGTGC
ACATGCTTTACATGTGTTTAGTCGAGGTTAAAAAAACGTCTAGGCCCCCCGAACCACGGGGACG
TGGTTTTCCTTTGAAAAACACGATGATAATATGGCCACAACCATGTCTAGAATGGTGAGCAAGG
GCGAGGAGCTGTTCACCGGGGTGGTGCCCATCCTGGTCGAGCTGGACGGCGACGTAAACGGC
CACAAGTTCAGCGTGTCCGGCGAGGGCGAGGGCGATGCCACCTACGGCAAGCTGACCCTGAA
GTTCATCTGCACCACCGGCAAGCTGCCCGTGCCCTGGCCCACCCTCGTGACCACCCTGACCTA
CGGCGTGCAGTGCTTCAGCCGCTACCCCGACCACATGAAGCAGCACGACTTCTTCAAGTCCGC
CATGCCCGAAGGCTACGTCCAGGAGCGCACCATCTTCTTCAAGGACGACGGCAACTACAAGAC
CCGCGCCGAGGTGAAGTTCGAGGGCGACACCCTGGTGAACCGCATCGAGCTGAAGGGCATCG
ACTTCAAGGAGGACGGCAACATCCTGGGGCACAAGCTGGAGTACAACTACAACAGCCACAAC
GTCTATATCATGGCCGACAAGCAGAAGAACGGCATCAAGGTGAACTTCAAGATCCGCCACAAC
ATCGAGGACGGCAGCGTGCAGCTCGCCGACCACTACCAGCAGAACACCCCCATCGGCGACGG
CCCCGTGCTGCTGCCCGACAACCACTACCTGAGCACCCAGTCCGCCCTGAGCAAAGACCCCA
ACGAGAAGCGCGATCACATGGTCCTGCTGGAGTTCGTGACCGCCGCCGGGATCACTCTCGGC eGF

ATGGACGAGCTGTACAAGTAAGTCGAC

Figure 15
control transfection
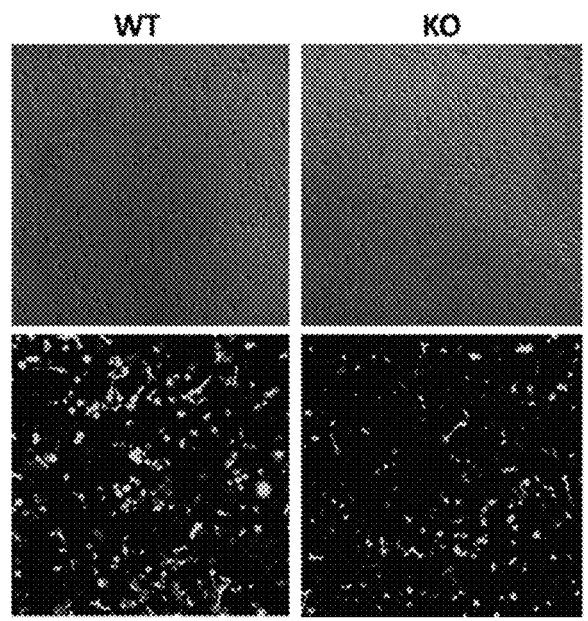
IRES dependent expression clone 174
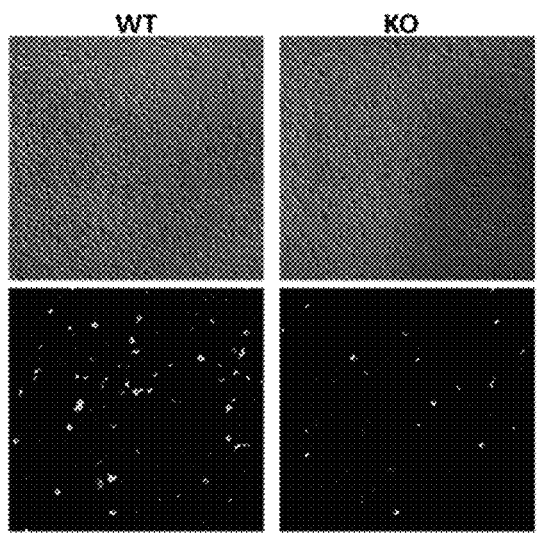
IRES dependent expression clone 215
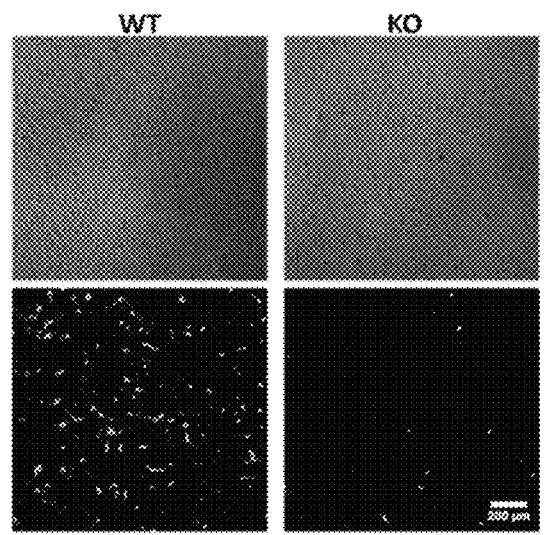

Figure 16

Experiment 1

| | WT (wild-type) efficiency [%] | Keratin 13 -/- efficiency [%] |
|---|---|---|
| Selective expression system 1 | 30 | 10 |
| Relative | 1 | 33% |

Experiment 2

| | WT (wild-type) efficiency [%] | Keratin 13 -/- efficiency [%] |
|---|---|---|
| Selective expression system 2, clone 01 | 32 | 15 |
| Selective expression system 2, clone 02 | 31 | 15 |
| Mean value | 31.5 | 15 |
| Relative | | 48% |
| Selective expression system 3, clone 01 | 46 | 16 |
| Selective expression system 3, clone 02 | 44 | 16 |
| Mean value | 45 | 16 |
| Relative | | 35% |

| | Relative |
|---|---|
| Mean value over all experiments | 39% |
| Stability value over all experiments | 8% |

SEQUENCE LISTING

<160> NUMBER OF SEQ ID NOS: 7

<210> SEQ ID NO 1
<211> LENGTH: 402
<212> TYPE: DNA
<213> ORGANISM: Hepatitis C virus

<400> SEQUENCE: 1

```
gccagccccc gattgggggc gacactccac catagatcac tcccctgtga ggaactactg      60
tcttcacgca gaaagcgtct agccatggcg ttagtatgag tgtcgtgcag cctccaggac     120 ccccctccc gggagagcca tagtggtctg cggaaccggt gagtacaccg gaattgccag      180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaacgt aacaccaacc gccgcccaca gg                        402
```

<210> SEQ ID NO 2
<211> LENGTH: 459
<212> TYPE: DNA
<213> ORGANISM: Artificial Sequence
<220> FEATURE:
<223> OTHER INFORMATION: IRES sequence (position 6 in Fig. 6) with 3
      stabilizing elements

<400> SEQUENCE: 2

```
gccagccccc gattgggggg ccagcccccg attgggggc cagcccccga ttggggggcc       60
agcccccgat tggggcgac actccaccat agatcactcc cctgtgagga actactgtct     120
tcacgcagaa agcgtctagc catggcgtta gtatgagtgt cgtgcagcct ccaggacccc     180
ccctcccggg agagccatag tggtctgcgg aaccggtgag tacaccggaa ttgccaggac     240
gaccgggtcc tttcttggat caacccgctc aatgcctgga gatttgggcg tgccccgcg      300 agactgctag ccgagtagtg ttgggtcgcg aaaggccttg tggtactgcc tgatagggtg     360
cttgcgagtg ccccgggagg tctcgtagac cgtgcaccat gagcacgaat cctaaacctc     420
aaagaaaaac caaacgtaac accaaccgcc gcccacagg                            459
```

<210> SEQ ID NO 3
<211> LENGTH: 498
<212> TYPE: DNA
<213> ORGANISM: Artificial Sequence
<220> FEATURE:
<223> OTHER INFORMATION: Primary IRES sequence (position 6 in Fig. 8)
      with 3 stabilizing elements (position 5 in Fig. 8, underlined) and
      linkers (position 4a in Fig. 8, boxed)

<400> SEQUENCE: 3

-continued

| | |
|---|---|
| ataaataaat aaaataaata aataaaataa ataaataaag ccagcccccg attggggggc | 60 |
| cagcccccga ttggggggcc agccccgat tgggggggcca gccccgatt ggggggcgaca | 120 |
| ctccaccata gatcactccc ctgtgaggaa ctactgtctt cacgcagaaa gcgtctagcc | 180 |
| atggcgttag tatgagtgtc gtgcagcctc caggaccccc cctcccggga gagccatagt | 240 |
| ggtctgcgga accggtgagt acaccggaat tgccaggacg accgggtcct ttcttggatc | 300 |
| aacccgctca atgcctggag atttgggcgt gccccgcga gactgctagc cgagtagtgt | 360 |
| tgggtcgcga aaggccttgt ggtactgcct gatagggtgc ttgcgagtgc cccgggaggt | 420 |
| ctcgtagacc gtgcaccatg agcacgaatc ctaaacctca agaaaaacc aaacgtaaca | 480 |
| ccaaccgccg cccacagg | 498 |

<210> SEQ ID NO 4
<211> LENGTH: 507
<212> TYPE: DNA
<213> ORGANISM: Artificial Sequence
<220> FEATURE:
<223> OTHER INFORMATION: Primary IRES sequence (position 6 in Fig. 10)
      with 3 stabilizing elements (position 5 in Fig. 10, underlined),
      linkers (position 4a in Fig. 8, boxed) and blockers

<400> SEQUENCE: 4

| | |
|---|---|
| cccaacacta taaataaata aaataaataa ataaaataaa taaataaagc cagcccccga | 60 |
| ttggggggcc agccccgat tgggggggcca gccccgatt ggggggccag ccccgattg | 120 |
| gggcgacac tccaccatag atcactcccc tgtgaggaac tactgtcttc acgcagaaag | 180 |
| cgtctagcca tggcgttagt atgagtgtcg tgcagcctcc aggaccccc ctcccggag | 240 |
| agccatagtg gtctgcggaa ccggtgagta caccggaatt gccaggacga ccgggtcctt | 300 |
| tcttggatca acccgctcaa tgcctggaga tttgggcgtg ccccgcgag actgctagcc | 360 |
| gagtagtgtt gggtcgcgaa aggccttgtg gtactgcctg atagggtgct tgcgagtgcc | 420 |
| ccgggaggtc tcgtagaccg tgcaccatga gcacgaatcc taaacctcaa gaaaaacca | 480 |
| aacgtaacac caaccgccgc ccacagg | 507 |

<210> SEQ ID NO 5
<211> LENGTH: 1619
<212> TYPE: DNA
<213> ORGANISM: Artificial Sequence
<220> FEATURE:
<223> OTHER INFORMATION: Nucleotide sequence of the functional system
      for the selective expression of target sequences in defined cell
      types (Keratin 13)

<400> SEQUENCE: 5

| | |
|---|---|
| acgcaccggt cggcctcctc ccagctggca agagccaccc ccgaaaccac ctccatagct | 60 |
| ggcagaggag ctctgcaggc ggaggctcat gaattcgtta tgttatgacc ttgctcgtca | 120 |
| agaagacagt tatgttatta aaagtcaggt cggatcaagc catagtacgg aaaaaactat | 180 |
| gctacctgtg agccccgtcc aaggacgtgc ggccgctaaa agaagtcagg ccatcacaaa | 240 |
| tgccacagct tgagtaaact gtgcagcctg tagctccacc tgagaaggtg taaaaaagtt | 300 |
| atgttatgga tccccccct aacgttactg gccgaagccg cttggaataa ggccggtgtg | 360 |
| cgtttgtcta tatgttattt tccaccatat tgccgtcttt tggcaatgtg agggcccgga | 420 |
| aacctggccc tgtcttcttg acgagcattc ctagggtct ttcccctctc gccaaggaa | 480 |
| tgcaaggtct gttgaatgtc gtgaaggaag cagttcctct ggaagcttct tgaagacaaa | 540 |
| caacgtctgt agcgacccct tgcaggcagc ggaaccccc acctggcgac aggtgcctct | 600 |

```
gcggccaaaa gccacgtgta taagatacac ctgcaaaggc ggcacaaccc cagtgccacg      660
ttgtgagttg gatagttgtg gaaagagtca aatggctctc ctcaagcgta ttcaacaagg      720
ggctgaagga tgcccagaag gtaccccatt gtatgggatc tgatctgggg cctcggtgca      780
catgctttac atgtgtttag tcgaggttaa aaaacgtcta ggccccccga accacgggga      840
cgtggttttc ctttgaaaaa cacgatgata atatggccac aaccatgtct agaatggtga      900
gcaagggcga ggagctgttc accggggtgg tgcccatcct ggtcgagctg gacggcgacg      960
taaacggcca caagttcagc gtgtccggcg agggcgaggg cgatgccacc tacggcaagc     1020
tgaccctgaa gttcatctgc accaccggca agctgcccgt gccctggccc accctcgtga     1080
ccaccctgac ctacggcgtg cagtgcttca gccgctaccc cgaccacatg aagcagcacg     1140
acttcttcaa gtccgccatg cccgaaggct acgtccagga gcgcaccatc ttcttcaagg     1200
acgacggcaa ctacaagacc cgcgccgagg tgaagttcga gggcgacacc ctggtgaacc     1260
gcatcgagct gaagggcatc gacttcaagg aggacggcaa catcctgggg cacaagctgg     1320
agtacaacta caacagccac aacgtctata tcatggccga caagcagaag aacggcatca     1380
aggtgaactt caagatccgc cacaacatcg aggacggcag cgtgcagctc gccgaccact     1440
accagcagaa cacccccatc ggcgacggcc ccgtgctgct gcccgacaac cactacctga     1500
gcacccagtc cgccctgagc aaagacccca acgagaagcg cgatcacatg gtcctgctgg     1560
agttcgtgac cgccgccggg atcactctcg gcatggacga gctgtacaag taagtcgac     1619

<210> SEQ ID NO 6
<211> LENGTH: 2164
<212> TYPE: DNA
<213> ORGANISM: Artificial Sequence
<220> FEATURE:
<223> OTHER INFORMATION: Nucleotide sequence of the functional system
      with an alternative antisense sequence for the selective
      expression of target sequences in defined cell types

<400> SEQUENCE: 6
acgcaccggt tgatgtcggc ctccacgctc tggcgcaggg ccagctcatt ctcatacttg       60
agcctgaagt cgtccgcagc cagcctggca ttgtcaatct ccaggatgac ccggttgttt      120
tcaatggtgg cggtcaggat cttgtcccgg agctcttcaa tggtcttgta gtagggctg      180 tagtcccgct cagggctagc tgggctctgc ttcaggtgcc agtcacggat cttcacctcc      240
aggtcagcgt tggcctcctc cagggcgcgc accttctcca ggtaggaagc caggcggtcg      300
ttgaggttct gcatggtgat cttctcattg ccagtgagga ggccgccatc acaagcacca      360
aagtcaacaa agccaccagc aaaaccccca ccaaagccac ctccaaggcc acctccatag      420
ccacctccaa ggccacctcc atagccacct ccaaagccac taccagcccc tccaccaaaa      480
ccacagctca cgccgcctcc atagccccca gctgatcccc cagacacaaa ccgagttgaa      540
caggtagaga caccacggcc tcctcccagc tggcaagagc caccccgaa accacctcca      600 tagctggcag aggagctctg caggcggagg ctcatgaatt cgttatgtta tgaccttgct      660
cgtcaagaag acagttatgt tattaaaagt caggtcggat caagccatag tacggaaaaa      720
actatgctac ctgtgagccc cgtccaagga cgtgcggccc ctaaaagaag tcaggccatc      780
acaaatgcca cagcttgagt aaactgtgca gcctgtagct ccacctgaga aggtgtaaaa      840
aagttatgtt atggatcccc cccctaacgt tactggccga agccgcttgg aataaggccg      900
gtgtgcgttt gtctatatgt tattttccac catattgccg tcttttggca atgtgagggc      960
```

```
ccggaaacct ggccctgtct tcttgacgag cattcctagg ggtctttccc ctctcgccaa       1020
aggaatgcaa ggtctgttga atgtcgtgaa ggaagcagtt cctctggaag cttcttgaag       1080
acaaacaacg tctgtagcga ccctttgcag gcagcggaac cccccacctg gcgacaggtg       1140
cctctgcggc caaaagccac gtgtataaga tacacctgca aaggcggcac aaccccagtg       1200
ccacgttgtg agttggatag ttgtggaaag agtcaaatgg ctctcctcaa gcgtattcaa       1260
caaggggctg aaggatgccc agaaggtacc ccattgtatg ggatctgatc tggggcctcg       1320
gtgcacatgc tttacatgtg tttagtcgag gttaaaaaac gtctaggccc cccgaaccac       1380
ggggacgtgg ttttcctttg aaaaacacga tgataatatg ccacaaccca tgtctagaat       1440
ggtgagcaag ggcgaggagc tgttcaccgg ggtggtgccc atcctggtcg agctggacgg       1500
cgacgtaaac ggccacaagt tcagcgtgtc cggcgagggc gagggcgatg ccacctacgg       1560
caagctgacc ctgaagttca tctgcaccac cggcaagctg cccgtgccct ggcccaccct       1620
cgtgaccacc ctgacctacg gcgtgcagtg cttcagccgc taccccgacc acatgaagca       1680
gcacgacttc ttcaagtccg ccatgcccga aggctacgtc caggagcgca ccatcttctt       1740
caaggacgac ggcaactaca agacccgcgc cgaggtgaag ttcgagggcg acaccctggt       1800
gaaccgcatc gagctgaagg gcatcgactt caaggaggac ggcaacatcc tggggcacaa       1860
gctggagtac aactacaaca gccacaacgt ctatatcatg gccgacaagc agaagaacgg       1920
catcaaggtg aacttcaaga tccgccacaa catcgaggac ggcagcgtgc agctcgccga       1980
ccactaccag cagaacaccc ccatcggcga cggccccgtg ctgctgcccg acaaccacta       2040
cctgagcacc cagtccgccc tgagcaaaga ccccaacgag aagcgcgatc acatggtcct       2100
gctggagttc gtgaccgccg ccgggatcac tctcggcatg gacgagctgt acaagtaagt       2160
cgac                                                                  2164
```

<210> SEQ ID NO 7
<211> LENGTH: 2175
<212> TYPE: DNA
<213> ORGANISM: Artificial Sequence
<220> FEATURE:
<223> OTHER INFORMATION: Nucleotide sequence of the functional system
      with an alternative antisense sequence and an alternative blocker
      sequence for the selective expression of target sequences in
      defined cell types

<400> SEQUENCE: 7

```
acgcaccggt tgatgtcggc ctccacgctc tggcgcaggg ccagctcatt ctcatacttg        60
agcctgaagt cgtccgcagc cagcctggca ttgtcaatct ccaggatgac ccggttgttt       120
tcaatggtgg cggtcaggat cttgtcccgg agctcttcaa tggtcttgta gtaggggctg       180
tagtcccgct cagggctagc tgggctctgc ttcaggtgcc agtcacggat cttcacctcc       240
aggtcagcgt tggcctcctc cagggcgcgc accttctcca ggtaggaagc caggcggtcg       300
ttgaggttct gcatggtgat cttctcattg ccagtgagga ggccgccatc acaagcacca       360
aagtcaacaa agccaccagc aaaaccccca ccaaagccac ctccaaggcc acctccatag       420
ccacctccaa ggccacctcc atagccacct ccaaagccac taccagcccc tccaccaaaa       480
ccacagctca cgccgcctcc atagccccca gctgatcccc cagacacaaa ccgagttgaa       540
caggtagaga caccacggcc tcctcccagc tggcaagagc cacccccgaa accacctcca       600
tagctggcag aggagctctg caggcggagg ctcatgaatt cgttatgtta tgaactgctt       660
ccttcacgac attcaacaga ccttgttatg ttattaaaag tcaggtcgga tcaagccata       720
```

```
gtacggaaaa aactatgcta cctgtgagcc ccgtccaagg acgtgcggcc gctaaaagaa      780
gtcaggccat cacaaatgcc acagcttgag taaactgtgc agcctgtagc tccacctgag      840
aaggtgtaaa aaagttatgt tatggatccc ccccctaacg ttactggccg aagccgcttg      900
gaataaggcc ggtgtgcgtt tgtctatatg ttattttcca ccatattgcc gtcttttggc      960
aatgtgaggg cccggaaacc tggccctgtc ttcttgacga gcattcctag gggtctttcc     1020
cctctcgcca aaggaatgca aggtctgttg aatgtcgtga aggaagcagt tcctctggaa     1080
gcttcttgaa gacaaacaac gtctgtagcg acccttttgca ggcagcggaa cccccacct    1140 ggcgacaggt gcctctgcgg ccaaaagcca cgtgtataag atacacctgc aaaggcggca     1200
caaccccagt gccacgttgt gagttggata gttgtggaaa gagtcaaatg gctctcctca     1260
agcgtattca acaaggggct gaaggatgcc cagaaggtac cccattgtat gggatctgat     1320
ctggggcctc ggtgcacatg ctttacatgt gtttagtcga ggttaaaaaa cgtctaggcc     1380
ccccgaacca cggggacgtg gttttccttt gaaaaacacg atgataatat ggccacaacc     1440
atgtctagaa tggtgagcaa gggcgaggag ctgttcaccg gggtggtgcc catcctggtc     1500
gagctggacg gcgacgtaaa cggccacaag ttcagcgtgt ccggcgaggg cgagggcgat     1560
gccacctacg gcaagctgac cctgaagttc atctgcacca ccggcaagct gcccgtgccc     1620
tggcccaccc tcgtgaccac cctgacctac ggcgtgcagt gcttcagccg ctaccccgac     1680
cacatgaagc agcacgactt cttcaagtcc gccatgcccg aaggctacgt ccaggagcgc     1740
accatcttct tcaaggacga cggcaactac aagacccgcg ccgaggtgaa gttcgagggc     1800
gacaccctgg tgaaccgcat cgagctgaag ggcatcgact tcaaggagga cggcaacatc     1860
ctggggcaca gctggagta caactacaac agccacaacg tctatatcat ggccgacaag     1920
cagaagaacg gcatcaaggt gaacttcaag atccgccaca acatcgagga cggcagcgtg     1980
cagctcgccg accactacca gcagaacacc cccatcggcg acggccccgt gctgctgccc     2040
gacaaccact acctgagcac ccagtccgcc ctgagcaaag accccaacga gaagcgcgat     2100
cacatggtcc tgctggagtt cgtgaccgcc gccgggatca ctctcggcat ggacgagctg     2160
tacaagtaag tcgac                                                     2175
```

SYSTEM AND METHOD FOR CELL TYPE-SPECIFIC TRANSLATION OF RNA MOLECULES IN EUKARYOTES

The present invention relates to methods and RNA constructs for the targeted translation of a polypeptide of interest into a eukaryotic target cell, and to the use thereof in therapeutic clinical applications.

BACKGROUND OF THE INVENTION

The directed introduction of certain molecules, for example medically and pharmacologically relevant proteins or cell vitality-influencing peptides in cancer treatment, is one of the greatest necessities in modern cell biology, but is also a difficulty in this field that has not yet been satisfactorily resolved.

Various techniques have been used to release and activate molecules of interest in a targeted manner in complex organisms such as humans. Two different approaches are of particular interest here.

Based on carrier systems such as liposomes (D. Papahadjopoulos, M. Moscarello, E. H. Eylar, T. Isac, Biochim. Biophys. Acta. 1975, 401, p. 317), molecules (e.g. cancer therapeutic agents) are coupled to or embedded in these carrier systems. Subsequently, the thus functionalized carrier systems are introduced into the body, where the introduction may include either the entire body or only certain parts of the organism. In this case, the carrier systems are ideally provided such that natural body conditions do not influence the stability between the carrier system and the molecule of interest and therefore the release of the molecule is omitted. External factors can now destabilize the carrier systems and thereby induce the release and thus activity of the incorporated molecules. As external factors for the release, local heating of certain body regions (hyperthermia approach) and light- or pH-induced cleavage of specific bonds between the carrier system and the molecule are used. All of these systems are summarized in principle by Qiu and Park (Advanced Drug Delivery Reviews 53 (2001) pp. 321-339 Environment-sensitive hydrogels for drug delivery) and Shamay and colleagues (Biomaterials, Light induced drug delivery into cancer cells 2011 32: pp. 1377-86). However, it is particularly problematic in all of these methods that the functional molecules must be introduced into the entire body at a high concentration and this can often lead to side effects and non-specific releases. In addition, the methodologies operate in a site-specific, but not cell type-specific, manner and thus for example cytostatic agents, in addition to the intended cancer cells, also damage surrounding tissue or are also rapidly distributed from the site of release in the body. Here, too, high doses must be used.

As a second methodology for the targeted release of molecules, systems are usually used in which the molecules of interest are coupled either directly or again by means of carrier systems to ligands which have a high specificity to certain surface molecules of defined cell types. Highly expressed surface receptors of cancer cells such as GPRCs or folate receptors are thus bound by the ligands (Lappano R, Maggiolini M., Nat Rev Drug Discov. 2011, 10: pp. 47-60, G protein-coupled receptors: novel targets for drug discovery in cancer; Sudimack J, Lee R J., Adv Drug Deliv Rev. 2000, 41: pp. 147-62. Targeted drug delivery via the folate receptor). After the ligands are bound to the surface receptors, bound molecules can either directly exhibit their activity (for example, radiopharmaceuticals or MRI contrasting reagents) or can exhibit their function (e.g. chemotherapeutic agents or DNA vectors) after phagocytotic uptake into the cells. However, this method also has significant disadvantages, which relate to the again relatively high total concentration in the entire body system, but also have to do specifically with the fact that most surface receptors have no absolute specificity for individual cell types or disease patterns and therefore coupling to such receptors may be associated with increased side effects in healthy tissues. In addition, a variety of specific receptors do not induce phagocytotic uptake of the bound carrier systems after coupling, and therefore these carrier systems remain outside the cells.

The largest number of biotechnologically, pharmacologically and medically relevant molecules for targeted transfer into defined cell types/tissues are peptides or proteins that are typically encoded at the DNA level. After introduction of these DNA molecules, these molecules are transported into the cell nucleus and subsequently, via a highly conserved mechanism, initially transcribed (transcription) into RNA molecules, post-transcriptionally modified and then transported out of the cell nucleus to be re-described within the cytoplasm by a highly conserved mechanism (translation) in amino acid sequences. Both the transcriptional and the translational mechanisms are identical with regard to the basic mechanism in all eukaryotic organisms and cell types. This means that, although with varying efficiency, each DNA sequence coding for a peptide generates the same primary product in each cell, which primary product can be subsequently further modified. The overall process of transcription and translation is called expression. Some RNA molecules remain untranslated and have a separate function.

Selective, targeted expressions of DNA sequences are possible if the coding region of a DNA segment is dependently regulated by cell type-specific or organ-specific promoter and enhancer sequences as well as degree of differentiation and maturation. Such sequences regulate the binding of the transcription apparatus and thus cause its activation only under defined environmental conditions. However, it is disadvantageous for this type of targeted expression of DNA constructs that 1) DNA constructs can be highly efficiently and homogeneously introduced into all cells within an organism or a tissue only with great difficulty, 2) DNA constructs for the subsequent transcription always have to be transported into the cell nucleus and interact there with the natural genetic material, as a result of which mutations and subsequent diseases (e.g. cancer) can arise, and 3) organ-specific promoter regions are often very large and so are not suitable for use in externally introduced DNA constructs.

As an alternative to using DNA constructs to express amino acid-based molecules, the step of nuclear transcription can be bypassed by directly introducing RNA molecules into cells or cell tissue. Works by different working groups were able to show (for a review article see: Van Tendeloo V F, Ponsaerts P, Berneman Z N. mRNA-based gene transfer as a tool for gene and cell therapy. Curr Opin Mol Ther. 2007; 9: pp. 423-431) that the introduction of RNA molecules takes place highly efficiently and rapidly without producing significant stress levels in the cells. Introduced RNA molecules remain in the cytoplasm of the cell and thus cannot interact negatively with the genome within the nucleus. Using conserved translation processes, introduced mRNA molecules and endogenously (naturally) present mRNA molecules are converted into proteins or peptides. For this purpose, certain sequence motifs within an mRNA molecule are required, which can be found in textbooks (e.g.

Alberts et al., Molecular Biology of the Cell, 2011, Wiley-Blackwell) in detail and are shown in simplified form in FIG. 1. In this case, mRNA molecules typically comprise the following units:

1: cap: The cap structure is a chemical change in mRNA molecules in eukaryotes, which dramatically increases the stability of RNA and is important for the transport of RNA from the nucleus into the cytoplasm and the subsequent translation of the mRNAs by the ribosomes. This usually relates to a modified guanine nucleotide, which is linked to the head of the RNA during transcription of the gene via a rare 5'-5' phosphodiester bond.

2: untranslated 5' region: represents a nucleotide sequence arranged upstream of the coding sequence. The region begins at the transcription start point and ends directly before the translation start codon. Within this sequence there may be regulatory sequences that influence, for example via secondary structures, the stability of the mRNA or act as binding sites for protein. In addition, a ribosomal binding site is typically present.

3: coding sequence: The coding sequence contains the information for the protein to be produced by the mRNA. Said sequence begins directly with the translation start codon and ends with the translation stop codon. The nucleotide sequence of the coding sequence is predetermined by the amino acid sequence of the encoded protein within the context of the triplet code. Depending on the triplet used, the expression rate and the stability of the mRNA can be influenced.

4: 3' untranslated region: represents the region that adjoins the region coding for protein directly behind the translation stop codon. It comprises the entire region up to the start of polyadenylation. Within the untranslated 3' region, regulatory sequences may also be present which are of particular importance for the polyadenylation of RNA as well as for its stability and transport.

5: poly(A) tail: polyadenylation takes place by attaching adenine nucleotides to the 3' end of the mRNA based on a post-transcriptional modification of the mRNA by the poly(A) polymerase. The length of the poly(A) tail makes a vital contribution to the stability of the mRNA, as well as the fact that proteins bind to this sequence and the CAP interacts with the poly(A) tail.

Disadvantages of the use of externally introduced RNA molecules may, however, affect certain applications in that i) RNA molecules typically have a limited lifespan and thus the formation of proteins takes place only over a limited period of time. Since the basic mechanism of translation remains identical in all eukaryotes and existing cell types, ii) no targeted, i.e. organ or cell type-specific expression of mRNA molecules introduced into the whole organism, could be implemented previously.

Recent research results (Quabium and Krupp, Synthetic mRNAs for manipulating cellular phenotypes: an overview (2015) New Biotechnology, 32: pp. 229-235) now allow highly efficient, chemical modification of mRNA molecules at different levels in order to regulate and, if necessary, significantly increase the lifespan described in point i). Such modification includes the a) use of chemically modified cap sequences based on the naturally occurring cap m7G5'pppN. Examples of this are in Jamielity et al. Synthetic mRNA cap analogs with a modified triphosphate bridge—synthesis, applications and prospects (2010) New. J. Chem 34: pp. 829-844. On the one hand, such modifications increase translational efficiency by effectively binding subunits of the translation apparatus. On the other hand, they improve the stability of the mRNA molecules, presumably by the fact that nucleases can engage the mRNA less efficiently from the 5-end sides.

b) use of stable 5' and 3' untranslated regions. Typically, stability can be significantly influenced by using appropriate nucleotide sequences. Attachment of binding partners and formation of secondary structures by base pairing are the main reasons for stabilization.

c) use of chemically modified nucleotides. Nucleotides of this kind, such as 5-methylcytidine or pseudouridine, primarily affect the binding of endonucleases and thus prevent the rapid degradation of the mRNA molecules.

d) use of efficient polyadenylation sequences in the untranslated 3' region in order to obtain the longest possible polyadenylations.

The object of the present invention is, inter alia, to provide methods and RNA constructs which allow a defined expression of mRNA in specific cell types.

BRIEF DESCRIPTION OF THE INVENTION

The present invention relates to the use of complex RNA and messenger RNA (mRNA) molecules, which are protected against degradation, for the cell-selective expression of intracellularly active or secretable RNA fragments, peptides or proteins.

A first aspect of the present invention relates to methods for the targeted translation of a polypeptide of interest in a eukaryotic target cell, characterized by introducing an RNA construct into cells, the RNA construct having at least the following elements in the 5' to 3' direction:

(a) an anticodogenic element (a) that is complementary to at least a portion of an mRNA of a gene expressed by the target cell;
(b) a blocking element (b) that interacts with at least a portion of the translation initiator element (d) at the 3' position;
(c) a stabilizing element (c);
(d) a translation initiator element (d);
(e) a sequence (e) coding for the polypeptide of interest,
(f)

translation of the polypeptide of interest being prevented in a non-target eukaryotic cell by base pairing of the blocking element (b) with the translation initiator element (d), and translation of the encoded polypeptide taking place in a eukaryotic target cell due to processing of the RNA construct induced by the interaction of the anticodogenic element with the mRNA expressed by the target cell.

Another aspect of the present invention is directed to methods for the targeted translation of an amino acid sequence of any length, i.e. of a polypeptide of interest in a eukaryotic target cell, characterized by introducing an RNA construct into cells, the RNA construct having at least the following elements in the 5' to 3' direction:

(a) an anticodogenic element (a) that is complementary to at least a portion of an mRNA of a gene expressed by the target cell;
(b) a blocking element (b) which is complementary to, or in another way reversibly alters, its functionality in at least a portion of the translation initiator element (d) at the 3' position;
(c) a stabilizing element (c);
(d) a translation initiator element (d);
(e) a sequence (e) coding for the polypeptide of interest, translation of the polypeptide of interest being prevented in a non-target eukaryotic cell by base pairing or other interaction of the blocking element (b) with the translation initiator element (d), and translation of the encoded polypeptide taking place in a eukaryotic target cell due to processing (degradation) of the RNA construct induced by interaction of the anticodogenic element with an mRNA specifically expressed by the target cell. This processing is interrupted by the stabilizing element (c), which leads to activation of the translation initiation element (d).

Another aspect of the present invention is directed to RNA constructs for the targeted translation of a polypeptide of interest in a eukaryotic target cell, the RNA construct having at least the following elements in the 5' to 3' direction:
   (a) an anticodogenic element (a) that is complementary to at least a portion of an RNA of a DNA portion expressed by the target cell or induces the cell type-specific degradation;
   (b) a blocking element (b) that is complementary to or otherwise inhibits at least a portion of the translation initiator element (d) at the 3' position;
   (c) a stabilizing element (c) that limits the cell type-specific degradation of the RNA to a portion thereof;
   (d) a translation initiator element (d) that functions independently of the 5' cap and is active only in target cells;
   (e) a sequence (e) coding for the polypeptide of interest; translation of the polypeptide of interest being prevented in a non-target eukaryotic cell by base pairing or other interaction of the blocking element (b) with the translation initiator element (d), and translation of the encoded polypeptide in a eukaryotic target cell due to interaction of the anticodogenic element (a) with an RNA expressed by the target cell, specific processing of the RNA construct taking place, as a result of which the translation initiator element (d) is activated.

Further aspects of the present invention are the use of the methods described herein and RNA constructs in therapeutic clinical applications, in neoplasias, underlying immunological disorders and metabolic disorders. Furthermore, the methods and RNA constructs described herein are suitable for cell type-specifically expressing the necessary components for gene-editing and thus for treating germline diseases. In addition to these typical applications, adult stem cells (iPS, multi-, toti- or pluripotent) of mammals and their derived tissues may also serve as target cells in vitro. The tissue or single cells resulting from these cells can then be used both in vivo in humans and in drug development.

BRIEF DESCRIPTION OF THE DRAWINGS

FIG. 4A) is a schematic illustration of one embodiment of an RNA construct of the present invention before and after processing by anticodogenic interaction between element 3 and cell type-specific RNA. When bound to target RNA, the anticodogenic sequence element leads to degradation of motifs 1-4 by means of established mechanisms.

Figure 1:
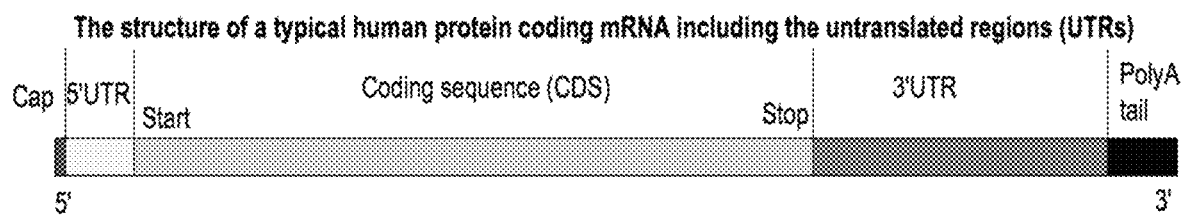
FIG. 1 is a schematic illustration of an mRNA molecule. All the portions of an mRNA may have a regulatory function for the stability of the molecule.

B) shows a calculated secondary structure of an exemplary functional IRES sequence (6) from HCV (HCV IRES 1b) according to SEQ ID No. 1, with the region from 289-311 omitted.

FIG. 5 shows a primary IRES nucleic acid sequence (HCV IRES 1b); position 6 in FIG. 4: SEQ ID NO: 1. The associated functional secondary structure is shown in FIG. 4.

FIG. 6A) is a schematic illustration of one embodiment of an RNA construct of the present invention before and after processing by anticodogenic interaction between element 3 and cell type-specific RNA. When bound to target RNA, the anticodogenic sequence element degrades motifs 1-4 by means of established mechanisms.

B) is a schematic illustration of the secondary structure of an exemplary IRES sequence (6) from HCV (HCV IRES 1b) with 3 stabilizing elements (5) according to SEQ ID No. 2, with the region from 346-368 omitted.

FIG. 7 shows a primary IRES sequence (position 6 in FIG. 6) with 3 stabilizing elements (position 5 in FIG. 6): SEQ ID NO: 2. The associated functional secondary structure is shown in FIG. 6.

FIG. 8A) is a schematic illustration of one embodiment of an RNA construct of the present invention before and after processing by anticodogenic interaction between element 3 and cell type-specific RNA. When bound to target RNA, the anticodogenic sequence element degrades motifs 1-4 by means of established mechanisms.

B) is a schematic illustration of the secondary structure of an exemplary IRES sequence (6) from HCV (HCV IRES 1b) with 3 stabilizing elements (5) and linkers (4a) according to SEQ ID No. 3, with the region from 384-407 omitted.

FIG. 9 shows a primary IRES sequence (position 6 in FIG. 8) with 3 stabilizing elements (position 5 in FIG. 8, underlined) and linkers (position 4a in FIG. 8, boxed): SEQ ID NO: 3. The associated functional secondary structure is shown in FIG. 8.

FIG. 10A) is a schematic illustration of one embodiment of an RNA construct of the present invention before and after processing by anticodogenic interaction between element 3 and cell type-specific RNA. When bound to target RNA, the anticodogenic sequence element degrades motifs 1-4 by means of established mechanisms.

B) is a schematic illustration of the secondary structure of an exemplary IRES sequence (6) from HCV (HCV IRES 1b) with 3 stabilizing elements (5), linkers (4a) and blockers (4b).

FIG. 11 shows a primary IRES sequence (position 6 in FIG. 10) with 3 stabilizing elements (position 5 in FIG. 10, underlined), linkers (position 4a in FIG. 8, boxed) and blockers (4b, bold): SEQ ID NO: 4. The associated secondary structure is shown in FIG. 10 according to SEQ ID No. 4, with the region from 402-420 omitted.

FIG. 12 shows an example of a nucleotide sequence of the functional system for the selective expression of target sequences in defined cell types according to SEQ ID No. 5, with the region from 1-4 omitted.

FIG. 13 shows an example of a nucleotide sequence of the functional system with an alternative antisense sequence for the selective expression of target sequences in defined cell types according to SEQ ID No. 6, with the regions from 1-4 and 1639-2164 omitted.

FIG. 14 shows an example of a nucleotide sequence of the functional system with an alternative antisense sequence and an alternative blocker sequence for the selective expression of target sequences in defined cell types according to SEQ ID No. 7, with the region from 1-4 omitted.

FIG. 15 shows microscopic images of cell type-dependent, blocker-IRES-controlled, selective expression of GFP.

FIG. 16 shows tables for the quantitative evaluation of the functional system for the selective expression of target genes.

The invention is described in more detail in the following on the basis of practical examples with reference to the drawings, without restricting the general inventive concept. In the drawings:

DETAILED DESCRIPTION OF THE INVENTION

The use of complex RNA and messenger RNA (mRNA) molecules, which are protected against degradation, for the cell-selective expression of intracellularly active or secretable RNA fragments, peptides or proteins is described. The basic structure of the RNA molecule includes stabilizing structures, a regulatory region and a functional region that codes for the sequence of interest. The regulatory structure acts as a constitutive inhibitor of the expression of the sequence of interest. The inhibition is only omitted when specific binding induces selective degradation of the regulatory portion, thus allowing expression of the sequence of interest.

The invention comprises the method and system for constructing suitable RNA sequences, using which it is possible, after introduction into any cell types, to induce the functionality of a target sequence, or of an amino acid-based structure resulting therefrom, only in defined cell types and to prevent this in all other cell types.

To solve the problem of defined expression of mRNA molecules in certain cell types after introduction into the whole organism or parts thereof, different sequence motifs are combined within the context of this patent application such that the functional translation of the sequence of interest is possible only in desired cell types, whereas this is not possible in other cell types. By adapting the sequence motifs, the cell type-dependent interaction between activation and inactivation can be adapted or completely reversed. In general, the system is arranged such that upstream sequences in the 5' region regulate the stability of the system and at the same time inhibit or generally regulate sequence motifs of interest in the 3' region. Inhibited sequences within the 3' region are in particular internal ribosomal entry site (IRES) sequences, which can serve as a secondary translation start. Inhibition by base pairing within the mRNA molecule is permanently maintained until the mRNA in suitable target cells encounters cell type-specific, endogenous mRNA molecules that form antisense-active base pairings with sequences in the 5' region of the introduced mRNA, thereby inducing degradation of the front region of the introduced mRNA. This abolishes the inhibition of the IRES and allows the expression of the target sequence. The cell type-specifically regulatable mRNA molecules are formed in detail according to the diagram shown in FIG. 2, which is explained in more detail below. In this case, as required, individual sequence motifs can also be omitted, swapped in their order, replaced by other motifs, or supplemented by other motifs.

Figure 2:
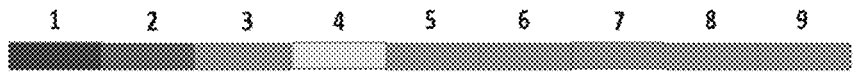
FIG. 2 is a schematic illustration of an embodiment of an RNA construct of the present invention for the selective expression of target sequences in specific cell types after the organ-wide or organism-wide introduction of the mRNA molecule.
Figure 3:
FIG. 3 is a schematic illustration of another embodiment of an RNA construct of the present invention for the selective expression of target sequences in specific cell types, where 1=CAP/modifications, 2=5' UTR, 3=anticodogenic fragment, 4=linker_IRES blocker linker, 5=stabilizing element, 6=IHRES, 7=sequence of interest, 8 and 9=3' UTR and poly(A).

FIG. 2 is a schematic illustration of an mRNA molecule for the selective expression of target sequences in specific cell types after organ-wide or organism-wide introduction of the mRNA molecule.

1) Optional use of a CAP sequence. This sequence may be a natural 7-methylguanosine (m7G) cap or may also contain chemical or other modifications. The CAP sequence serves to regulate the stability and translational efficiency of the primary sequence. For certain applications, such as the development of RNA molecules or RNA fragments with low stability, the CAP sequence can also be dispensed with.

2) Use of a 5' untranslated sequence. This sequence serves primarily to regulate the stability (half-life) of the introduced mRNA. Nucleotide sequences may either be of a synthetic nature or be taken from sequences of known genes. Depending on the stability required, additional sequences can be integrated into this region, individually or in combination, which regulate stability and the translation rate. Examples would be G-quadruplexes (high mRNA stability with simultaneously low translation rate) or binding sites for endonucleases (reduction of mRNA stability). The length of the 5' untranslated sequence is freely selectable and may be zero as required.

3) Subsequent to the 5' untranslated sequence, the actual regulatory cassette starts for the cell type-specific expression of artificially introduced mRNA molecules. The starting point is an antisense or RNAi-active anticodogenic sequence within the introduced mRNA against a gene expressed specifically in a desired cell type. If the mRNA construct is introduced into a cell in which the cell type-specific gene is not transcribed, no interaction takes place. However, if such a sense mRNA is present, there is a base pairing between the sense and antisense strand, as a result of which subsequent degradation of both the sense and the antisense strand is induced. The degradation itself is initiated and carried out by conserved protein complexes in all cells, in particular the enzyme complex RISC (RNA-induced silencing complex) and the ribonucleases Dicer and Drosha playing an important role (Sontheimer E J (2005). "Assembly and function of RNA silencing complexes." Nature Reviews Molecular Cell Biology. 6: pp. 127-138). Depending on the surrounding sequences, degradation may involve the entirety of the introduced mRNA strand or be limited by additional sequences.

Cell type-specific or organ-specific protein expression patterns are known as prior art based on modern transcriptome or proteome analyses for almost every cell type or tissue and can easily serve as a basis for a preselection (see, for example, Ko et al. PNAS, 2013, 110: pp. 3095-3100 or Whitfield et al. PNAS, 2003, 100: pp. 12319-12324).

To identify suitable anticodogenic elements (3) having the best possible antisense function, different parameters can be taken into consideration. See, by way of example: Elbashir S M, Harborth J, Lendeckel W, Yalcin A, Weber K, Tuschl T. Duplexes of 21-nucleotide RNAs mediate RNA interference in cultured mammalian cells. Nature. 2001 May 24; 411 (6836): pp. 494-8. Elbashir S M, Lendeckel W, Tuschl T. RNA interference is mediated by 21- and 22-nucleotide RNAs. Genes Dev. 2001 Jan. 15; 15 (2): pp. 188-200. Reynolds A, Leake D, Boese Q, Scaringe S, Marshall W S, Khvorova A. Rational siRNA design for RNA interference. Nat Biotechnol. 2004 March; 22 (3): pp. 326-30.

According to the invention, the following parameters should play a role in this case:

Anticodogenic sequence preferably 50 to 100 nt downstream of the start codon

Search for sequence motifs $AA(N_{19})TT$ or $NA(N_{21})$, or $NAR(N_{17})YNN$, with N=any nucleotide, R=purine and Y=pyrimidines Anticodogenic sequence preferably with G+C content of 35-60%

Avoidance of four or more identical nucleotides in succession

Avoidance of sequence motifs with high homology to other genes

4) The antisense/RNAi active sequence is followed by a sequence which is able to produce base pairings with or otherwise interact with the IRES or IRES-like sequence in the 3' region of the construct and therefore to function as an IRES blocker. Since IRES sequences themselves are also able to perform their function as CAP-independent translation initiators mainly to solely by means of specifically constructed secondary structures, the additional base pairings between the IRES blocker and IRES sequence change these sequences such that no IRES-dependent translation initiation occurs as long as the IRES blocker is present IRES blocking takes place at full length of the introduced mRNA. Since defined induced changes in the length of the mRNA occur only when binding the specific antisense/RNAi sequence to sense mRNA, the IRES activity is omitted in all cells that do not have a suitable sense mRNA. The presence of this sense mRNA in specific cell types leads, however, to antisense-sense binding and thereby to the induction of degradation of the introduced mRNA, as a result of which the sequence of the IRES blocker is affected and thus loses its blocking effect on the secondary-structure formation of the IRES sequence. The IRES blocker sequence is characterized in that it i) contains anticodogenic portions of the IRES sequence, binds to ii) one or more sequence sections of the IRES sequence, iii) can comprise spacer sequences between the IRES sequence anticodogenic portions, which spacer sequences can comprise compositions varying in length and nucleotide composition, iv) preferably binds to stem sequences or loop sequences of the IRES in order to alter the secondary structure thereof, v) in that the sequences have a variable length with respect to the IRES anticodogenic nucleotides without typically developing antisense or RNAi activity themselves. In this case, changes in the secondary structure of the IRES by means of the blocker can be only minimal in order to effectively disable the function of the IRES and to allow refolding of the IRES sequence upon degradation of the blocker. In order to allow the best possible binding of the IRES blocker and IRES, the sequence of the IRES blocker may be surrounded by both preceding and subsequent sequence motifs of linker sequences that can be varied in length.

5) In order to restrict the complete degradation of the introduced mRNA to specific areas thereof after binding of sense and antisense/RNAi mRNA motifs, mRNA sequence motifs must be incorporated which interrupt the degradation due to binding partners or secondary structures. Such sequence motifs may include hairpin loops or stem loops. They can be used in single or multiple alignment in both the 5' and the 3' direction for sense-antisense pairing. The use of sequence motifs, which are typically stabilized by secondary structures or binding partners, thus leads, in combination with the specific antisense/RNAi cassette in target cells with sense pairing, to the interruption of mRNA degradation and thereby to stabilization of the RNA motifs located in the 3' direction towards this sequence. Here, the stable secondary structures then assume the function of the CAP with respect to stabilization, but not with respect to translation initiation. In cells in which no sense-antisense pairing takes place, the total length of the mRNA is retained and the loop structures remain without significant function. Stable mRNA secondary structures can be linked to adjacent sequence motifs with or without connecting sequences (linkers).

6) Since the CAP sequence necessary for translation initiation is cleaved off in target cells, a CAP-independent ribosomal binding site must be integrated into the sequence behind the stable mRNA secondary structures in order to initiate peptide or protein formation. For this purpose, an IRES or comparable translational initiator sequence is incorporated in the 3' direction, which sequence typically allows the direct binding of ribosomal subunits due to its developed secondary structure. IRES sequences can be cellular, viral or synthetic. Due to IRES blocker sequences matching the IRES sequence in the same full-length mRNA construct, which blocker sequences prevent the formation of the IRES secondary structure necessary for translation initiation by base pairing, the IRES sequence is inactive in non-target cells and full-length mRNA present therewith. In target cells, by contrast, the degradation of the IRES blocking sequence takes place by sense-antisense/RNAi interaction whereby the functional IRES secondary structure is formed by energetically driven processes and can function for the translation of subsequent coding sequences. The IRES sequence can be incorporated with or without linker sequences to surrounding sequence motifs. Alternatively, nucleotide sequences that are not considered IRES, but can still act as translation initiators, can be used.

7) At the 3' position with respect to the IRES or IRES-like structure used, coding sequences can be introduced which are transcribed by means of translation into peptides or proteins. The translation of these sequence motifs takes place exclusively in cells in which the IRES sequence is active, i.e. in target cells in which endogenous sense sequences are also transcribed to the antisense/RNAi motif within the introduced mRNA. RNA sequences to be translated can code for any desired amino acid sequences and thus, for example, form therapeutically active peptides and proteins, toxins, antibodies, interleukins or surface receptors.

8) Subsequent to the defined translatable reading frame, further sequences are necessary in the 3' direction, which in turn ensure the stability of both the full-length mRNA and the mRNA that is truncated in target cells. These sequences include both the 3' untranslated region and the poly(A) tail, which tail is also characteristic of almost every endogenous mRNA. Depending on the need, endogenous or synthetic sequence motifs can be used. Depending on the desired stability of the mRNA construct, this can be adjusted in a targeted manner by appropriate choice of the sequence motif. In this case, i) formed secondary structures within the motif, ii) possible binding sites for stabilizing/destabilizing factors, and iii) the length of the poly(A) tail are particularly important.

Based on this system, selective adjustable expression of target sequences is possible for the first time even when mRNA molecules are introduced into the entire organism.

The RNA constructs of the present invention can be introduced into a target cell in a variety of ways. They can enter the cell by transfection, membrane fusion, electroporation or as a retroviral vector. For example, WO 02/44321 discloses the introduction of a foreign target gene into a cell.

In a particular embodiment of the present invention, interaction of the anticodogenic element (a) with the mRNA expressed by the target cell results in degradation or inactivation of the blocking element (b) such that translation of the polypeptide of interest can occur. In a further embodiment, the degradation of the mRNA on the stabilizing element (c) is stopped.

In further preferred embodiments of the invention, the anticodogenic element (a) has one or more of the following features and has the following function or functions after introduction into the target cell:
  (i) attachment to an RNA sequence specific for the target cell.
  (ii) formation of double-stranded RNA hybrids of freely adjustable length
  (iii) induction of cellular degradation of the introduced RNA construct in the region of the double-stranded RNA hybrid.

In further preferred embodiments of the invention, the blocking element (b) has one or more of the following features:
  (i) the function of the translation initiator element is suppressed.
  (ii) the blocking element can be degraded or inactivated under suitable conditions.
  (iii) the suppressive function on the translation initiator element is reversible after inactivation or degradation of the blocking element.
  (iv) the blocking element performs its function by base pairing in or near the sequence of the translation initiator element, thereby changing the secondary structure thereof.
  (v) the blocking element performs its function by causing other molecules to directly or indirectly inhibit the translation initiator element.

In further preferred embodiments of the invention, the stabilizing element (c) has one or more of the following features:
  (i) nucleotide sequence that prevents the degradation of RNA in the 3' direction by exo- and/or endonucleases.
  (ii) nucleotide sequence, characterized in that it forms stabilizing secondary structures, such as stem-loops.
  (iii) nucleotide sequence, characterized in that stabilizing elements such as peptides or proteins bind to the RNA.
  (iv) nucleotide sequence, characterized in that molecules bind to the RNA and perform a chemical, stabilizing modification of the RNA 5' end.

In further preferred embodiments of the invention, the translation initiator element (d) has one or more of the following features:
  (i) cell-type-dependent, selective inhibition of the function of translation initiation
  (ii) functionality exclusively upon degradation or inactivation of the components of the regulatory cassette (elements a and b)
  (iii) functionality exclusively in target cells, while the translation initiator element is inactive in all other cell types.
  (iv) induction of translation irrespective of the cap structure in the 5' region of the initial RNA construct
  (v) induction of translation by means of direct or indirect binding of ribosomal subunits or complete ribosomes (e.g. IRES sequences).
  (vi) induction of translation by formation or release of specific secondary structures after omission of inhibition by the blocking element
  (vii) induction of translation by attachment of specific molecules or chemical modification after omission of inhibition by the blocking element In particularly preferred embodiments of the present invention, the RNA construct has a combination of anticodogenic and IRES-dependent expression regulation.

The degradation of the blocking element can take place, for example, via the system of antisense- or siRNA-dependent mRNA degradation. The phenomenon known from the literature as "RNA interference" (RNAi) is based on the fact that short RNA molecules (siRNA, small interfering RNA) in the cell can interact with messenger RNA (mRNA) (literature: Fire A., Xu S., Montgomery M. K., Kostas S. A., Driver S. E., Mello C. C., Nature Feb. 19, 1998; 391 (6669): pp. 744-745). Due to a complex mechanism that is controlled by enzymes (for example via the DICER and RISC complex), there is degradation of the mRNA. In addition to the siRNA, other small RNA species were discovered, such as the "microRNAs" (miRNA) or "short hairpin RNAs" (shRNA), which can also inhibit protein expression by means of related mechanisms.

The translation initiation of the RNA construct into the target cell induced by the degradation and/or inactivation of the blocking element is a complex process involving the concerted interaction of numerous factors (Pain, V. M., 1996, Eur. J. Biochem. 236, pp. 747-771). For most mRNAs, the first step is to recruit ribosomal 40S subunits to the RNA at or near the 5' end thereof (FIG. 1). The association of 40S with the mRNA is made much easier by the cap-binding complex eIF4F. Factor eIF4F consists of three subunits: the RNA helicase eIF4A, the cap binding protein eIF4E and the multiadaptor protein eIF4 G, which acts as a framework for the proteins in the complex and binding sites for eIF4E, eIF4a, eIF3 and has a poly(A)-binding protein.

Infection of cells with a variety of RNA viruses results in the selective inhibition of translation of mRNA of the host but not of the virus. For example, infection of cells with poliovirus, a cytoplasmic RNA virus, results in the modification of a plurality of translation initiation factors. In particular, the proteolysis of both forms of eIF4G, eIF4GI and eIF4GII (Gradi et al. 1998, Proc. Nat. Acad. Sci. USA 95, pp. 11089-11094) by virus-encoded proteases leads to the inhibition of translation of most cellular mRNAs having a cap. In contrast, the translation of poliovirus mRNAs containing a specific sequence as IRES in the 5' UTR, which sequence comprises 450 nucleotides and can recruit 40S subunits in the absence of intact eIF4F, is not inhibited (Jang et al. 1988 J. Virol. 62, pp. 2363-2643). IRES elements have been found in picornaviral, flaviviral, pestiviral, retroviral, lentiviral, and insect viral RNA and in animal cellular RNA. Overviews of known IRES sequence motifs represent the state of scientific knowledge (presented as an overview on: www.iresite.org (as of Feb. 2, 2017)). IRES-containing animal mRNAs can recruit ribosomal subunits both via their 5' cap end and via their IRES elements. As a result, translation is possible under conditions under which the cap-dependent translation is reduced, e.g. during a viral infection, during the G2/M phase of the cell cycle, apoptosis or stress conditions (Johannes et al. (1999), Proc. Natl. Acad. Sci. USA 96, pp. 13118-13123; Cornelis et al. (2000), molecular Cell 5, pp. 597-605; Pyronnet et al. (2000), molecular Cell 5, pp. 607-616; Stein et al., 1998, Mol. and Cell. Biol. 18, pp. 3112-3119; Holcik et al., 2000, Oncogene 19, pp. 4174-4177; Stoneley et al., 2000, mol. and Cell. Biol. 20, pp. 1162-1169). Up to 3% of the cellular mRNAs of animals are translated at a reduced concentration of the cap-binding complex eIF4F (Johannes et al., 1999).

For the RNA constructs of the present invention, a plurality of different IRES elements can be used as the translation initiator element. For example, the prior art describes IRES elements used for cap-independent expression of foreign genes in linear multicistronic mRNA in animal cells (U.S. Pat. Nos. 6,060,273; 6,114,146; 5,358,856; 6,096,505; 171,821; 5,766,903), in plant cells (WO 98/54342) and, more generally, in eukaryotic cells (U.S. Pat. Nos. 171,821; 5,766,903; 5,925,565; 6,114,146).

For example, the secondary structure of the IRES element remains unaffected and thus functional and is changed (=inactivated) only by a suitable choice of the blocking element (b).

In further preferred embodiments of the invention, the RNA construct has one or more of the following optional features:
  (i) 5' cap sequence, in order to increase the stability of the entire mRNA construct
  (ii) 5' untranslated region, in order to be able to regulate the stability of the entire mRNA construct and to suppress the 5' cap induced translation (e.g. incorporation of quadruplex sequences)
  (iii) 3' untranslated region, in order to increase the stability of the entire mRNA construct and of the processed mRNA partial fragment in target cells.
  (iv) poly(A) region, in order to increase the stability of the entire mRNA construct and of the processed mRNA partial fragment in target cells.
  (v) all elements of the entire mRNA construct of claims 1 to 8 may contain linker sequences of any length within the element itself or between the individual elements. Linker sequences can be functionless and are used for the pure spatial separation of the individual elements, or for integrating additional functions into the system.

PRACTICAL EXAMPLES

1.) Nucleotide Sequence of the Functional System for the Selective Expression of Target Sequences in Defined Cell Types (FIG. 12)

By means of standard molecular biological procedures (PCR, ligation and transformation), a short sequence of the keratin 13 gene (marked above with short KERATIN) of the human genome was linked as antisense to what is known as a LOOP sequence. The LOOP sequence includes linker sequences that are conducive to the flexibility of the construct, a blocker sequence, and nucleotide sequences that form stable secondary structures (LOOPs). While the blocker sequence is able to interact with sequence portions of the IRES through base pairing and thereby alter the secondary structure thereof, the secondary structures of the LOOPs cause an interruption of exo-nuclease activity (see Chapman et al., eLife, 2014, 3: e01892). Subsequent sequence portions represent the IRES of the encephalomyocarditis virus (Bochkov and Palmenberg, BioTechniques, 2006, 41: pp. 283-292) and the coding sequence of the green fluorescent protein (eGFP). If the blocker sequence is omitted, the IRES allows the translation of subsequent sequences—in this case, the eGFP, which was chosen here for reasons of easy detectability. The blocker sequence is omitted only if a complementary sense sequence to the antisense sequence (short KERATIN) in the selected cell type is present for binding.

2.) Nucleotide Sequence of the Functional System with an Alternative Antisense Sequence for the Selective Expression of Target Sequences in Defined Cell Types (FIG. 13)

By means of standard molecular biological procedures (PCR, ligation and transformation), a long sequence of the keratin 13 gene (marked above with KERATIN) of the human genome was linked as antisense to what is known as a LOOP sequence. The LOOP sequence includes linker sequences that are conducive to the flexibility of the construct, a blocker sequence, and nucleotide sequences that form stable secondary structures (LOOPs). While the blocker sequence is able to interact with sequence portions of the IRES through base pairing and thereby alter the secondary structure thereof, the secondary structures of the LOOPs cause an interruption of exo-nuclease activity (see Chapman et al., eLife, 2014, 3: e01892). Subsequent sequence portions represent the IRES of the encephalomyocarditis virus (Bochkov and Palmenberg, BioTechniques, 2006, 41: pp. 283-292) and the coding sequence of the green fluorescent protein (eGFP). If the blocker sequence is omitted, the IRES allows the translation of subsequent sequences—in this case, the eGFP, which was chosen here for reasons of easy detectability. The blocker sequence is omitted only if a complementary sense sequence to the antisense sequence (KERATIN) in the selected cell type is present for binding.

3.) Nucleotide Sequence of the Functional System with an Alternative Antisense Sequence and an Alternative Blocker Sequence for the Selective Expression of Target Sequences in Defined Cell Types (FIG. 14)

By means of standard molecular biological procedures (PCR, ligation and transformation), a long sequence of the keratin 13 gene (marked above with KERATIN) of the human genome was linked as antisense to what is known as a LOOP sequence. The LOOP sequence includes linker sequences that are conducive to the flexibility of the construct, a blocker sequence, and nucleotide sequences that form stable secondary structures (LOOPs). While the blocker sequence is able to interact with sequence portions of the IRES through base pairing and thereby alter the secondary structure thereof, the secondary structures of the LOOPs cause an interruption of exo-nuclease activity (see Chapman et al., eLife, 2014, 3: e01892). Subsequent sequence portions represent the IRES of the encephalomyocarditis virus (Bochkov and Palmenberg, BioTechniques, 2006, 41: pp. 283-292) and the coding sequence of the green fluorescent protein (eGFP). If the blocker sequence is omitted, the IRES allows the translation of subsequent sequences—in this case, the eGFP, which was chosen here for reasons of easy detectability. The blocker sequence is omitted only if a complementary sense sequence to the antisense sequence (KERATIN) in the selected cell type is present for binding.

4.) Cell Type-Dependent, Blocker IRES-Controlled, Selective Expression of GFP (FIG. 15)

Mouse epidermal cells (keratinocytes) with (WT) and without (knockout keratin 13 mutant=KO) keratin 13 mRNA were treated with GFP expression plasmids as a positive control. After 24 h, the cells were examined using light microscopy (gray) and fluorescence microscopy (green). As a result of the transmission, a uniformly high expression of GFP can be seen in both cell lines.

By using the constructs generated in FIG. 1 (clone 174) and 2 (clone 215), the expression of GFP takes place highly preferably in those cells expressing keratin 13 mRNA and barely takes place in the cells deleted for the keratin 13 gene.

This effect is justified by the fact that in the absence of keratin 13 mRNA, the blocking sequence within the generated mRNA construct interacts with the IRES sequence and, by altering the IRES secondary structure, suppresses its function and thus GFP expression. In contrast, in the presence of keratin 13 mRNA (WT), the generated mRNA construct is degraded by sense-antisense interaction as far as the loops, as a result of which the blocker sequence disappears. As a result, the function of the IRES is enabled and the GFP is expressed.

5.) Quantitative Evaluation of the Functional System for the Selective Expression of Target Genes (FIG. 16)

Wild-type and keratin 13 mutant cells were, as described in FIG. 4, loaded with the different functional systems. After 24 hours, the expression level of the selected target protein GFP was measured in all cells by means of flow cytometry. At least 5000 cells were evaluated for each measurement. All differences between WT and keratin 13−/− mutations are highly significant.

The invention claimed is:

1. Method for the targeted translation of a polypeptide of interest in a eukaryotic target cell, characterized by introducing an RNA construct into cells, the RNA construct having at least the following elements in the 5' to 3' direction:
   (a) an antisense sequence (a) that is complementary to at least a portion of an mRNA of a gene expressed by the target cell;
   (b) a blocking element (b) that interacts with at least a portion of the translation initiator element (d);
   (c) a stabilizing element (c), wherein the stabilizing element is a nucleotide sequence that prevents degradation of RNA in the 3' direction from the stabilizing element (c) by exonucleases, the stabilizing element (c) comprising binding partners and/or secondary structures configured to restrict complete degradation of the RNA in the 3' direction from the stabilizing element (c);
   (d) a translation initiator element (d);
   (e) a sequence (e) coding for the polypeptide of interest, translation of the polypeptide of interest being prevented in a non-target eukaryotic cell by base pairing of the blocking element (b) with the translation initiator element (d), and translation of the encoded polypeptide taking place in a eukaryotic target cell due to processing of the RNA construct induced by interaction of the antisense sequence with the mRNA expressed by the target cell.

2. Method according to claim 1, wherein interaction of the antisense sequence (a) with the mRNA expressed by the target cell results in degradation or inactivation of the blocking element (b) such that translation of the polypeptide of interest can occur.

3. Method according to claim 2, wherein the degradation of mRNA on the stabilizing element (c) is stopped.

4. Method according to claim 1, characterized in that the antisense sequence (a) has one or more of the following features:
   (i) formation of double-stranded RNA hybrids of freely adjustable length;
   (ii) induction of cellular degradation of the introduced RNA construct in the region of the double-stranded RNA hybrid.

5. Method according to claim 1, characterized in that the blocking element (b) has one or more of the following features:
   (i) the blocking element (b) can suppress function of the translation initiator element (d)

(ii) the blocking element (b) can be degraded or inactivated when the antisense sequence (a) interacts with the mRNA of the gene expressed by the target cell;

(iii) the suppressive function on the translation initiator element (d) is reversible after inactivation or degradation of the blocking element (b).

6. Method according to claim 1, characterized in that the stabilizing element (c) has a nucleotide sequence, characterized in that said nucleotide sequence forms stabilizing secondary structures.

7. Method according to claim 1, characterized in that the translation initiator element (d) has one or more of the following features:

(i) when included in the RNA construct, having cell-type-dependent selective inhibition of the function of translation initiation;

(ii) functionality exclusively upon degradation or inactivation of the components of antisense sequence (a) and/or blocking element (b);

(iii) functionality exclusively in target cells, in which endogenous sense sequences to the antisense sequence (a) are transcribed, while the translation initiator element is inactive in all other cell types;

(iv) induction of translation irrespective of a cap structure in the 5' region of the initial RNA construct;

(v) induction of translation by means of direct or indirect binding of ribosomal subunits or complete ribosomes;

(vi) induction of translation by formation of specific secondary structures necessary for translation initiation after omission of inhibition by the blocking element (b).

8. Method according to claim 1, characterized in that the RNA construct has one or more of the following features:

(i) 5' cap sequence, in order to increase the stability of the entire mRNA construct;

(ii) 5' untranslated region, in order to be able to regulate the stability of the entire mRNA construct and to suppress a 5' cap induced translation;

(iii) 3' untranslated region, in order to regulate the stability of the entire mRNA construct and of a processed mRNA partial fragment from degradation interrupted by the stabilizing element (c) that leads to activation of the translation initiator element (d) in target cells;

(iv) poly(A) region, in order to regulate the stability of the entire mRNA construct and of a processed mRNA partial fragment from degradation interrupted by the stabilizing element (c) that leads to activation of the translation initiator element (d) in target cells;

(v) the entire mRNA construct may contain linker sequences of any length within any of elements (a)-(e) or between the individual elements.

9. An RNA construct for the targeted translation of a polypeptide of interest in a eukaryotic target cell, wherein the RNA construct has at least the following elements in the 5' to 3' direction:

(a) an antisense sequence (a) that is complementary to at least a portion of an mRNA of a gene expressed by the target cell;

(b) a blocking element (b) that is complementary to or otherwise inhibits at least a portion of the translation initiator element (d);

(c) a stabilizing element (c) wherein the stabilizing element (c) is a nucleotide sequence that prevents degradation of RNA in the 3' direction from the stabilizing element (c) by exonucleases, the stabilizing element (c) comprising binding partners and/or secondary structures configured to restrict complete degradation of the RNA in the 3' direction from the stabilizing element (c);

(d) a translation initiator element (d) that functions independently of 5' cap and is active only in target cells;

(e) a sequence (e) coding for the polypeptide of interest;

wherein the RNA construct is configured such that translation of the polypeptide of interest is prevented in a non-target eukaryotic cell when the RNA construct is in said non-target eukaryotic cell by base pairing of the blocking element (b) with the translation initiator element (d), and translation of the encoded polypeptide in a eukaryotic target cell takes place when the RNA construct is in said eukaryotic target cell due to processing of the RNA construct induced by interaction of the antisense sequence (a) with the mRNA expressed by the target cell as a result of which the translation initiator element is activated.

10. The RNA construct according to claim 9, characterized in that the antisense sequence (a) has one or more of the following features:

(i) formation of double-stranded RNA hybrids of freely adjustable length;

(ii) induction of cellular degradation of the introduced RNA construct in the region of the double-stranded RNA hybrid.

11. The RNA construct according to claim 9, characterized in that the blocking element (b) has one or more of the following features:

(i) the blocking element (b) can be degraded or inactivated when the antisense sequence (a) interacts with the mRNA of the gene expressed by the target cell;

(ii) suppressive function on the translation initiator element (d) is reversible after inactivation or degradation of the blocking element.

12. The RNA construct according to claim 9, characterized in that the stabilizing element (c) has:

a nucleotide sequence, characterized in that said nucleotide sequence forms stabilizing secondary structures.

13. The RNA construct according to claim 9, characterized in that the translation initiator element (d) has one or more of the following features:

(i) when included in the RNA construct, having cell-type-dependent selective inhibition of the function of translation initiation;

(ii) functionality exclusively upon degradation or inactivation of the antisense sequence (a) or the blocking element (b);

(iii) functionality exclusively in target cells, in which endogenous sense sequences to the antisense sequence (a) are transcribed, while the translation initiator element is inactive in all other cell types;

(iv) induction of translation irrespective of a cap structure in the 5' region of the initial RNA construct;

(v) induction of translation by means of direct or indirect binding of ribosomal subunits or complete ribosomes;

(vi) induction of translation by formation of specific secondary structures necessary for translation initiation after omission of inhibition by the blocking element.

14. The RNA construct according to claim 9, characterized in that the RNA construct has one or more of the following optional features:

(i) 5' cap sequence, in order to increase the stability of the entire mRNA construct;

(ii) 5' untranslated region, in order to be able to regulate the stability of the entire mRNA construct and to suppress a 5' cap induced translation;

(iii) 3' untranslated region, in order to regulate the stability of the entire mRNA construct and of a processed mRNA partial fragment from a degradation interrupted by the stabilizing element (c) that leads to activation of the initiation element (d) in target cells;
(iv) poly(A) region, in order to regulate the stability of the entire mRNA construct and of a processed mRNA partial fragment from a degradation interrupted by the stabilizing element (c) that leads to activation of the translation initiator element (d) in target cells;
(v) the entire mRNA construct may contain linker sequences of any length within any of elements (a)-(e) or between the individual elements.

* * * * *